(12) United States Patent
Gilligan et al.

(10) Patent No.: US 9,358,091 B2
(45) Date of Patent: *Jun. 7, 2016

(54) TWO-DIMENSIONAL BAR CODES IN ASSISTED REPRODUCTIVE TECHNOLOGIES

(71) Applicant: INGURAN, LLC, Navasota, TX (US)

(72) Inventors: Thomas B. Gilligan, College Station, TX (US); Sam Hogue, College Station, TX (US); Juan Moreno, College Station, TX (US); Johnathan Charles Sharpe, Hamilton (NZ)

(73) Assignee: Inguran, LLC, Navasota, TX (US)

( * ) Notice: Subject to any disclaimer, the term of this patent is extended or adjusted under 35 U.S.C. 154(b) by 56 days.

This patent is subject to a terminal disclaimer.

(21) Appl. No.: 14/057,743

(22) Filed: Oct. 18, 2013

(65) Prior Publication Data

US 2014/0046126 A1 Feb. 13, 2014

Related U.S. Application Data

(63) Continuation-in-part of application No. 13/448,948, filed on Apr. 17, 2012, now Pat. No. 8,865,379.

(60) Provisional application No. 61/809,739, filed on Apr. 8, 2013, provisional application No. 61/803,063, filed on Mar. 18, 2013, provisional application No. 61/715,741, filed on Oct. 18, 2012, provisional application No. 61/483,490, filed on May 6, 2011, provisional application No. 61/476,751, filed on Apr. 18, 2011.

(51) Int. Cl.
*G03C 1/73* (2006.01)
*A61D 19/04* (2006.01)
*B23K 26/00* (2014.01)
(Continued)

(52) U.S. Cl.
CPC .......... *A61D 19/024* (2013.01); *B23K 26/0084* (2013.01); *B29C 59/165* (2013.01); *B41J 2/442* (2013.01); *C12M 1/24* (2013.01); *G03C 1/73* (2013.01); *G03C 1/733* (2013.01); *G03C 5/56* (2013.01); *G06K 1/126* (2013.01); *B41M 5/24* (2013.01)

(58) Field of Classification Search
None
See application file for complete search history.

(56) References Cited

U.S. PATENT DOCUMENTS

| 3,507,281 A | 4/1970 | Cassou |
| 3,877,430 A | 4/1975 | Wieder |

(Continued)

FOREIGN PATENT DOCUMENTS

| DE | 19849543 A1 | 4/1999 |
| DE | 29816802 U1 | 2/2000 |

(Continued)

OTHER PUBLICATIONS

Witschi et al. "Utilization of bar code of trace semen from bulls to straws", ICAR2008 (presentation 8 pages, 16 slides, Jun. 2008).*

(Continued)

*Primary Examiner* — Martin Angebrandt
(74) *Attorney, Agent, or Firm* — Ryan Christensen; Hashim Rahman

(57) ABSTRACT

A container suitable for storing biological material which is laser etched with a two-dimensional bar code and methods for producing the same. The container can be in the form of a straw having a thickness between about 0.1 mm and about 0.3 mm or can be in the form of another container that holds multiple straws. The laser etched mark can be in the form of a two-dimensional bar code may be located on an exterior surface of the container, and when the container is a straw, it remains unwarped and impermeable to fluids.

33 Claims, 13 Drawing Sheets

(51) Int. Cl.

| | |
|---|---|
| B23K 26/08 | (2014.01) |
| A61D 19/02 | (2006.01) |
| B29C 59/16 | (2006.01) |
| G03C 5/56 | (2006.01) |
| C12M 1/24 | (2006.01) |
| B41M 5/26 | (2006.01) |
| B41J 2/44 | (2006.01) |
| G06K 1/12 | (2006.01) |
| B41M 5/24 | (2006.01) |

(56) References Cited

U.S. PATENT DOCUMENTS

| | | | |
|---|---|---|---|
| 4,990,792 | A | 2/1991 | Frei |
| 4,992,347 | A | 2/1991 | Hawkins et al. |
| 5,111,523 | A | 5/1992 | Ferlier et al. |
| 5,160,940 | A | 11/1992 | Cassou et al. |
| 5,289,767 | A | 3/1994 | Montalto et al. |
| 5,444,466 | A | 8/1995 | Smyczek et al. |
| 5,508,499 | A | 4/1996 | Ferrario |
| 5,558,449 | A | 9/1996 | Morgavi |
| 5,559,231 | A | 9/1996 | Yamamoto et al. |
| 5,560,845 | A | 10/1996 | Birmingham et al. |
| 5,671,667 | A | 9/1997 | Simmet |
| 6,303,673 | B1 | 10/2001 | Clarke et al. |
| 6,386,458 | B1 * | 5/2002 | Leiber et al. ................. 235/487 |
| 7,824,748 | B2 | 11/2010 | Dalvey et al. |
| 7,995,196 | B1 * | 8/2011 | Fraser ................ G06K 9/00577 356/71 |
| 8,196,807 | B2 | 6/2012 | Grimard |
| 8,865,379 | B2 * | 10/2014 | Sharpe et al. .................... 430/18 |
| 2001/0036537 | A1 | 11/2001 | Jux et al. |
| 2002/0067900 | A1 | 6/2002 | Mills et al. |
| 2003/0008234 | A1 | 1/2003 | Berneth et al. |
| 2003/0157475 | A1 | 8/2003 | Schenk |
| 2003/0174990 | A1 | 9/2003 | Andrieu et al. |
| 2004/0043308 | A1 | 3/2004 | Lutz et al. |
| 2005/0080358 | A1 | 4/2005 | Iwami et al. |
| 2005/0116046 | A1 | 6/2005 | Borgsmueller et al. |
| 2005/0218126 | A1 | 10/2005 | Leyvraz |
| 2006/0016543 | A9 | 1/2006 | Majumdar et al. |
| 2006/0057555 | A1 | 3/2006 | Damari et al. |
| 2006/0068315 | A1 | 3/2006 | Gore |
| 2006/0072444 | A1 | 4/2006 | Engel et al. |
| 2007/0113358 | A1 | 5/2007 | Rabolt et al. |
| 2007/0235414 | A1 | 10/2007 | Shah et al. |
| 2007/0269740 | A1 | 11/2007 | Blank et al. |
| 2008/0116105 | A1 * | 5/2008 | Statham ........................ 206/534 |
| 2008/0164873 | A1 | 7/2008 | Hoekstra et al. |
| 2008/0179301 | A1 | 7/2008 | Garty et al. |
| 2009/0093054 | A1 | 4/2009 | Sjogren et al. |
| 2009/0123992 | A1 | 5/2009 | Chin |
| 2009/0162531 | A1 | 6/2009 | Nesbitt |
| 2009/0181156 | A1 | 7/2009 | Nesbitt |
| 2009/0266804 | A1 | 10/2009 | Costin et al. |
| 2010/0000627 | A1 * | 1/2010 | Lecointe ........................ 141/18 |
| 2010/0015558 | A1 | 1/2010 | Jarvis et al. |
| 2010/0025387 | A1 | 2/2010 | Arai et al. |
| 2010/0141729 | A1 | 6/2010 | Petsch et al. |
| 2010/0198620 | A1 | 8/2010 | Mullenger et al. |
| 2011/0076712 | A1 | 3/2011 | Gilligan et al. |
| 2011/0130657 | A1 | 6/2011 | Chomas et al. |
| 2011/0176051 | A1 * | 7/2011 | Randers-Pehrson et al. . 348/349 |
| 2011/0239791 | A1 | 10/2011 | Fici |
| 2012/0021362 | A1 | 1/2012 | Jarvis et al. |
| 2012/0089490 | A1 | 4/2012 | Blaine |
| 2012/0263863 | A1 | 10/2012 | Nesbitt |
| 2014/0023813 | A1 | 1/2014 | Sharpe et al. |
| 2014/0046126 | A1 | 2/2014 | Gilligan et al. |

FOREIGN PATENT DOCUMENTS

| | | |
|---|---|---|
| EP | 0798118 B1 | 3/2002 |
| JP | 2004-321395 A | 11/2004 |
| WO | 2004101870 A2 | 11/2004 |
| WO | 2005109332 A1 | 11/2005 |
| WO | 2006018640 A1 | 2/2006 |
| WO | 2008031793 A1 | 3/2008 |
| WO | 2010023102 A1 | 3/2010 |
| WO | 2011012397 A1 | 2/2011 |

OTHER PUBLICATIONS

"Thermo Scientific matrix 2D barcoded storage tubes" (2 pages, © 2009).*
Holtz et al. "laser induced ablation of polymers using a patterned dopant generated form a leuco-dye precursopr via flood exposure: A 'portable conformable mask' approach to laser ablation of PMMA at 351 nm", Appl. Phys. A, vol. 60 pp. 529-535 (1985).*
Breeder's Journal Fall 2007 (18 pages) (2007).*
Synrad, "Marking 2D codes on FR4", (1 page) (Jul. 2003).*
Laser Systems India © 2011 (2 pages) (2011).*
Synrad "Marking circuit boards" (2 pages) (Feb. 2004).*
Synrad "Marking test tubes" (1 page) (Aug. 2002).*
ICAR letter to manufacturers of eartags, (33 pages) (May 2006).*
Aditus Consulting, "JpGraph Manual, chapter 26 Datamatrix (2D-barcode)" 7 pages (downloaded Sep. 2015, copyright Aug. 2009).*
Aditus Consulting, "JpGraph Manual, Version: 3.0.2 table of contents" 21 pages (downloaded Sep. 2015, copyright Aug. 2009).*
Benifla, Jean-Louis, et al., "Safety of cryopreservation straws for human gametes or embryos: a preliminary study with human immunodeficiency virus-1", Hum. Reprod. (2005) 15 (10): 2186-2189.
ESRF (The European Synchrotron) "Sample Support" Instruction for Beamlines, printed Dec. 10, 2012: http://www.esrf.eu/UsersAndScience/Experiments/MX/How_to_use_our_beamlines/Prepare_Your_Experiment/Sample_support (5 pp).
PCT Search Report dated Mar. 6, 2014, issued in corresponding PCT Application No. PCT/US2013/065684 (19 pp).
ESRF Canisters, Cryocane (Nov. 10, 2007); http://web.archive.org/web/20071101200033/http://www.esrf.eu/UsersAndScience/Experiments/MX/How_to_use_our_beamlines/Prepare_Your_Experiment/Sample_support.
US Office Action dated Sep. 9, 2015 for U.S. Appl. No. 14/110,117.
EP Examination Report dated Oct. 27, 2015 for U.S. Appl. No. 12774883.8.
US Final Office Action dated Dec. 30, 2015 for U.S. Appl. No. 14/110,117.
AU Examination Report dated Dec. 9, 2015 for AU Application No. 2013331042.
CN Office Action dated Dec. 7, 2015 for U.S. Appl. No. 201280018875.3.
Synrad, Inc., "Marking PVC tubing", Newsletter Issue 72, Oct. 2003, 3pp.
Synrad, Inc., "Contrasting marks in PVC" and "marking electrical connectors", Newsletter Issue 81, (first page) 3pp, (Feb. 2004).
Synrad, Inc., "Marking polyethylene dip tubes", Newsletter Issue 116, Jul. 2005, 3pp.
Synrad, Inc., "Marking common plastics", Newsletter Issue 86, Apr. 2004, 3pp.
"Animal Reproduction Technology-Bovine"; Minitube; 2010 (44pp).
PCT International Search Report and Written Opinion dated Aug. 3, 2012, issued in corresponding PCT Application No. PCT/US2012/033920 (20 pp).
Synrad, Inc., "Featured application: Laser marking curved or cylindrical surfaces", Newsletter Issue 243, Aug. 2010, 3pp.
Synrad, Inc., "Marking PVC tubing", Newsletter Issue 72, Oct. 2003, 3pp.
Synrad, Inc., "Contrasting marks in PVC" and "marking electrical connectors", Newsletter Issue 81, (first page) 3pp. (Feb. 2004).
Synrad, Inc., "Marking polythylene dip tubes", Newsletter Issue 116, Jul. 2005, 3pp.
Synrad, Inc., "Marking common plastics", Newletter Issue 86, Apr. 2004, 3pp.
Hofmann, et al., High contrast and intact surface—a challenge in laser marking of plastics, Proc. SPIE, vol. 774, 1987, pp. 156-180.

(56) References Cited

OTHER PUBLICATIONS

Marshall, Clif; "Integrated Field Data Transfer Using Bar Coded Semen Streaws"; Symposium, 2008, pp. 17-23; Proceedings of the 22nd Technical Conference on Artificial Insemination & Reproduction (7pp).

"Animal Reporduction Technology-Bovine"; Minitube; 2010 (44pp).

US Office Action dated dated Feb. 10, 2015 issued in corresponding U.S. Appl. No. 14/110,117.

US Office Action dated dated May 7, 2015 issued in corresponding U.S. Appl. No. 14/110,117.

US Notice of Allowance dated Feb. 8, 2016 for U.S. Appl. No. 14/110,117.

Canadian Examiner's Requisition dated Mar. 17, 2016 for CA Application No. 2,833,172.

Canadian Examiner's Requisition dated Apr. 4, 2016 for CA Application No. 2,888,458.

* cited by examiner

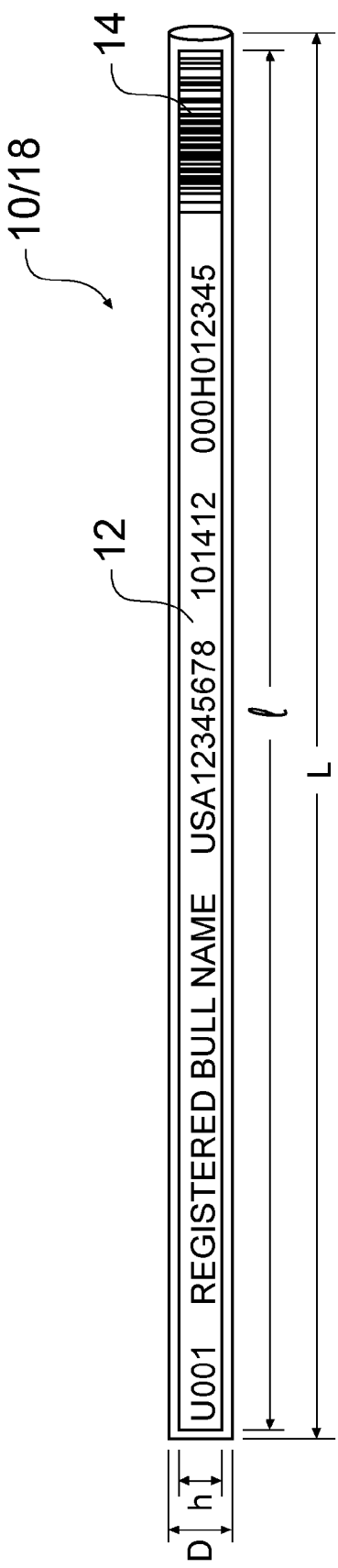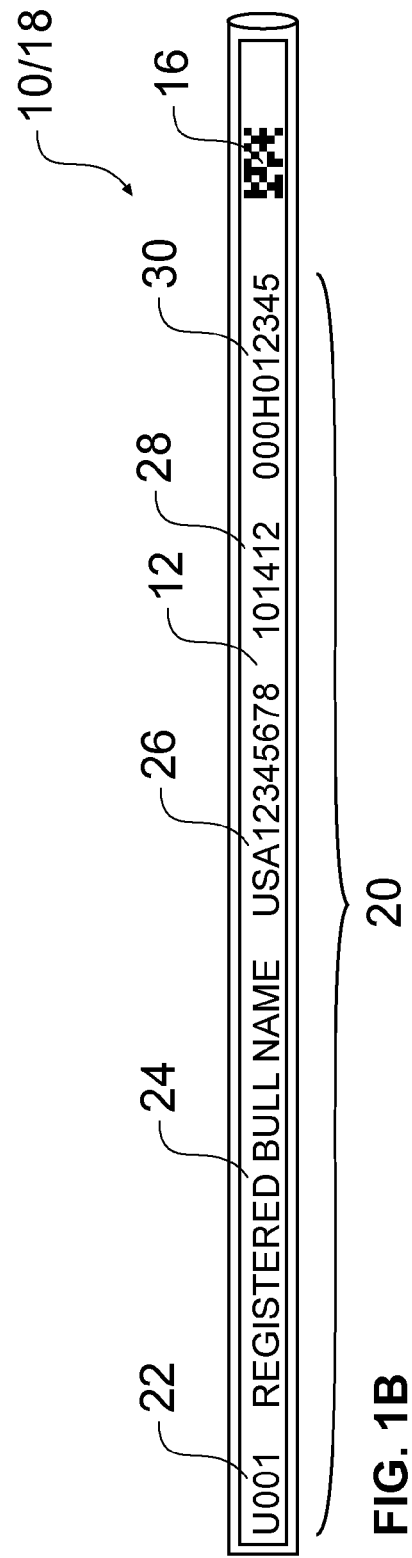
FIG. 1A
FIG. 1B

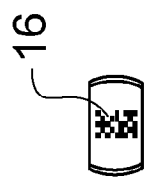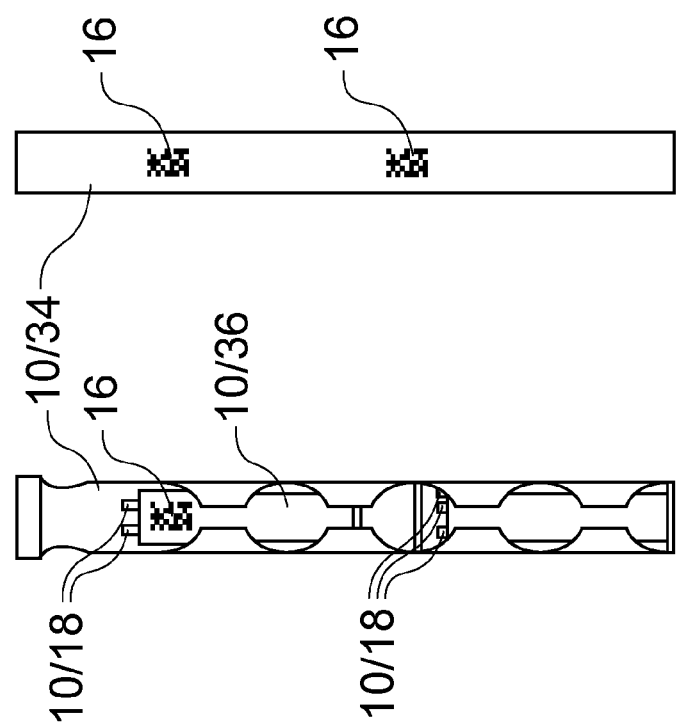

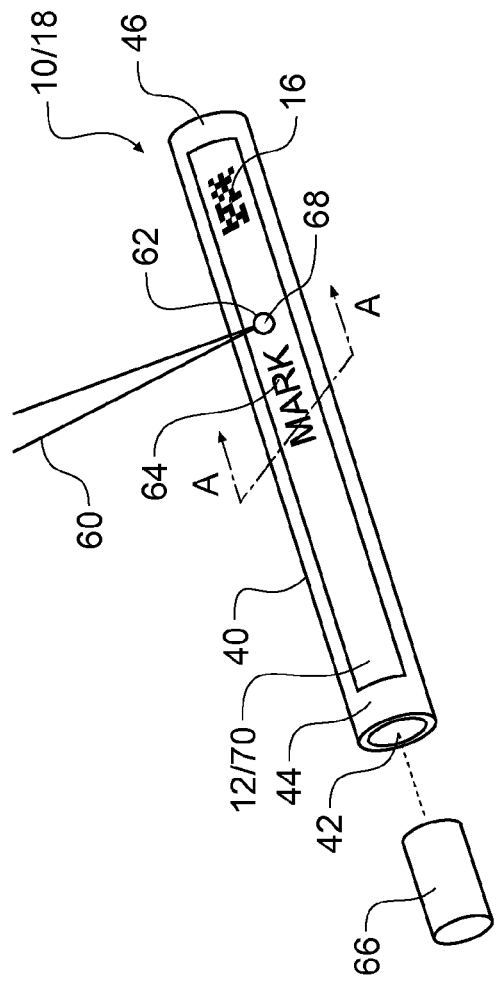
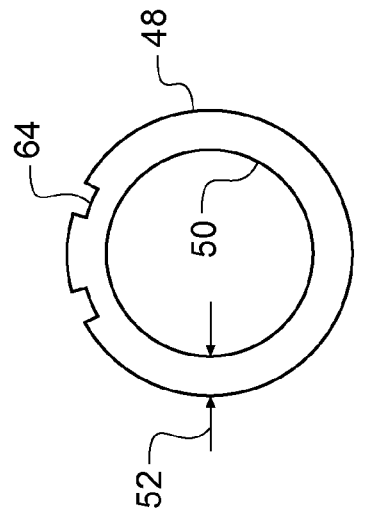

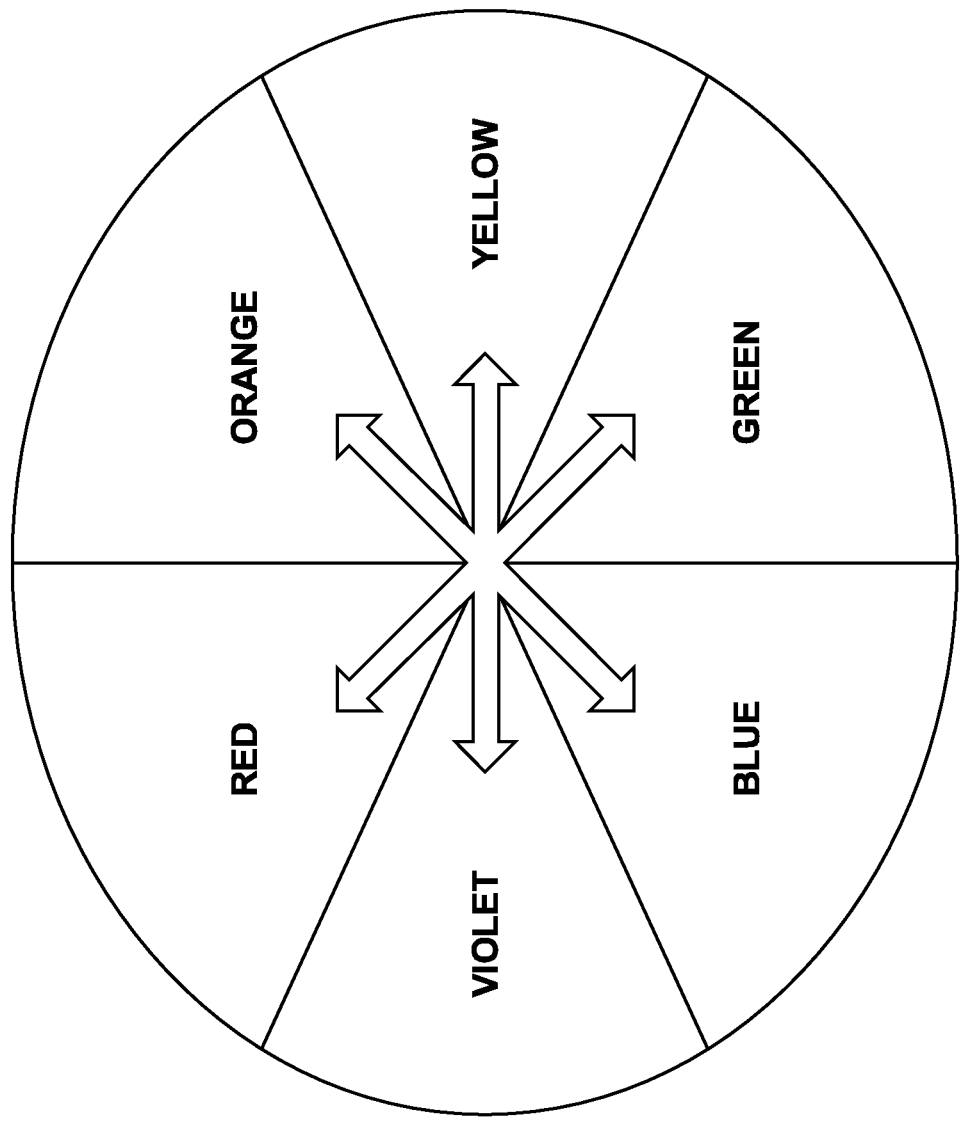

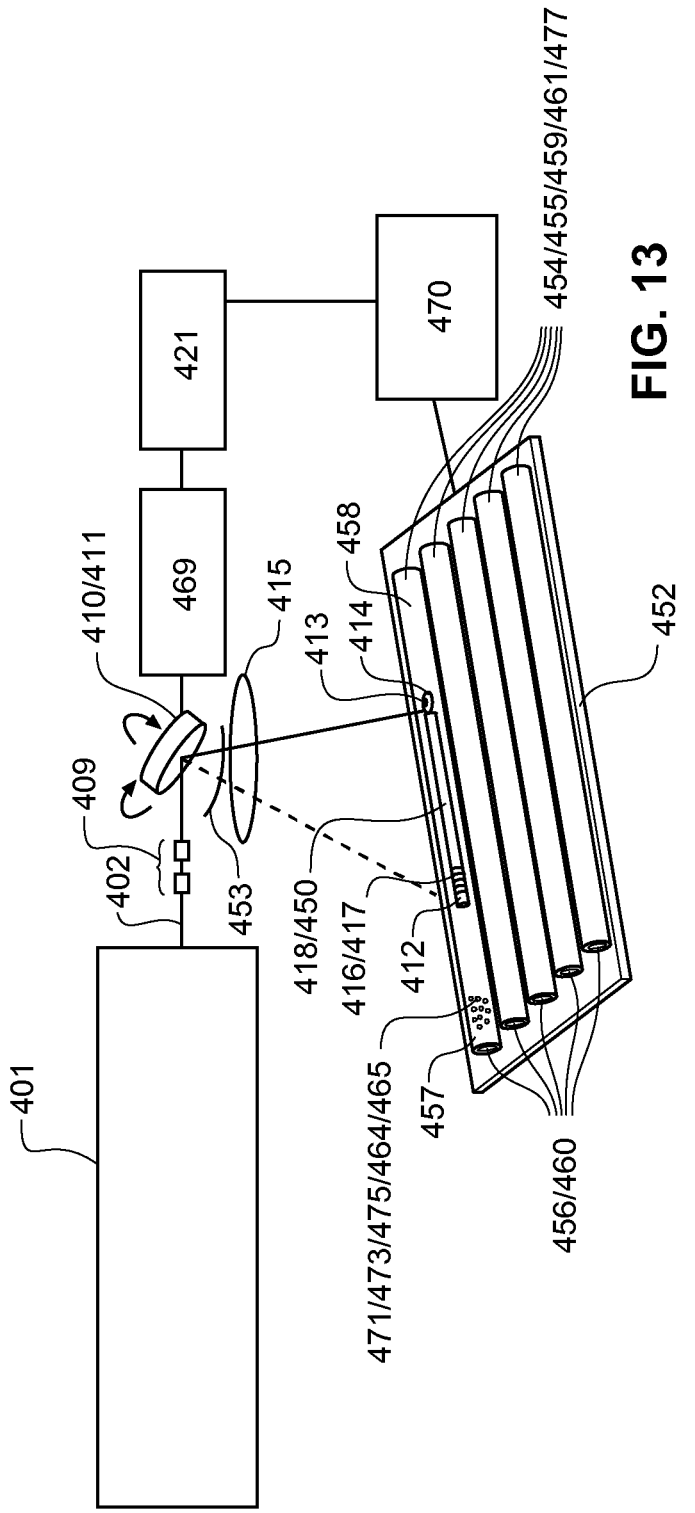

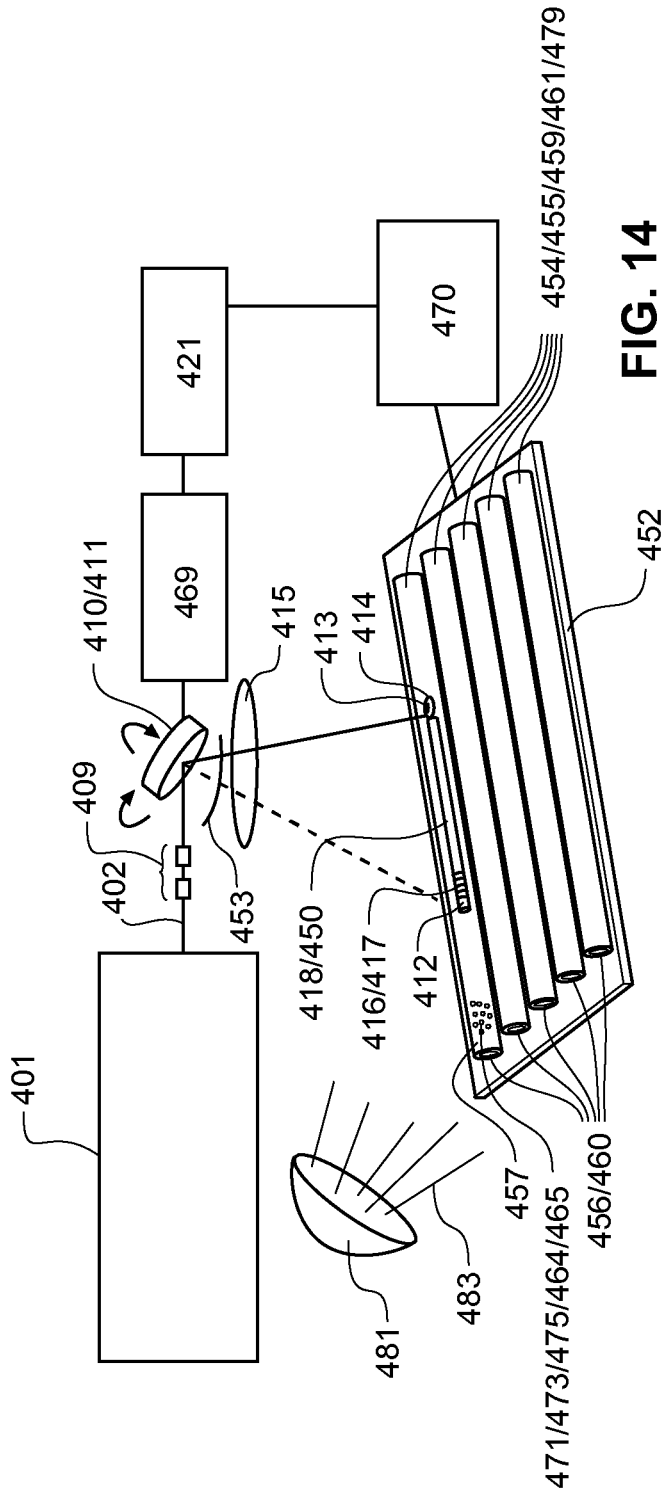

TWO-DIMENSIONAL BAR CODES IN ASSISTED REPRODUCTIVE TECHNOLOGIES

This application is a continuation-in-part of U.S. patent application Ser. No. 13/448,948, filed on Apr. 17, 2012 which itself claims the benefit of U.S. Provisional Patent Application No. 61/483,490, filed on May 6, 2011 and U.S. Provisional Patent Application No. 61/476,751, filed on Apr. 18, 2011, the entire contents of each of which are incorporated herein by reference. This application also claims the benefit of U.S. Provisional Patent Application No. 61/715,741, filed on Oct. 18, 2012, U.S. Provisional Patent Application No. 61/803,063, filed on May 18, 2013, and U.S. Provisional Patent Application No. 61/809,739, filed on Apr. 8, 2013, the entire contents of each of which are incorporated herein by reference.

BACKGROUND

This disclosure relates generally to assisted reproductive technologies, and more particularly relates to the incorporation of two-dimensional bar codes on containers for use in livestock reproduction.

In the field of assisted reproductive technologies, particularly in livestock, sperm is collected and identified with donor information. After processing, straws containing the biological material are generally labeled with identifying information relating to the mammal from which the sperm was collected as well as freeze lot and batch numbers. This information was previously printed on each straw with an ink jet printer, and transcribed or logged manually at the time inseminations were performed to track pregnancy, lineage and other genetic factors in potential offspring.

Depending on the types of cells contained therein, various regulatory bodies require certain information to be printed in readable manner on the container. Since sperm is often sold in French cryopreservation straws with volumes which are typically 0.5 ml or 0.25 ml there is often very little space for printing information. The required information may include: a 3-2-5 format (Stud-Breed-Sire No.) NAAB uniform code; the sires registered name; the sires registration Number; a date, lot number, batch number, or freeze code; international stud code; other processing info (stud #).

Most, if not all, authorities require that the prescribed information is readable to the naked eye. A 0.25 ml straw can have a length of about 133 mm and a diameter of about 1 mm or 2 mm, which provides a limited space for the six, or so, required fields of printed information. The limited area is further constricted by the additional limitations inherent in straw printing. For example, straws must be printed in a single pass because a second pass would require a precise realignment based on the location of the first text. Such a precise realignment is not possible in the hoppers which feed typical straw printing machines. As such, printing is generally limited to certain number of characters otherwise the characters become too crowded to read.

In addition to the readable identification information, a linear bar code has been suggested for tracking and transcribing straw information. However, due to existing straw printing limitations the bar code must be placed in line the other legally required text, resulting in a severely limited amount of available space. Linear bar codes provide a great deal of convenience by eliminating transcription time and errors since they can be scanned. However, linear bar codes are not necessarily a space efficient means for representing additional characters. As such, inline bar code printing has been limited to providing about 17 characters.

SUMMARY OF INVENTION

Certain embodiments of the claimed invention are summarized below. These embodiments are not intended to limit the scope of the claimed invention, but rather serve as brief descriptions of possible forms of the invention. The invention may encompass a variety of forms which differ from these summaries.

One embodiment relates to a method of inventory and data management for reproductive cells which may begin by obtaining reproductive cells which were derived from an identified source and which may continue by processing the reproductive cells. A container may be marked with a two-dimensional bar code by laser etching the two-dimensional bar code into the container. Processed reproductive cells from the identified source in the marked container, and the two-dimensional bar code etched in the container can identify the source of the reproductive cells.

Another embodiment relates to a straw for containing a biological material. The straw can include an axial body defining an axial passage between a pair of body ends. The axial body can have an exterior surface, and an interior surface separated by an axial body thickness between about 0.1 mm and about 0.3 mm. A laser etched mark in the form of a two-dimensional bar code may be located on the exterior surface of the axial body, whereas the straw remains unwarped and impermeable to fluids.

BRIEF DESCRIPTION OF THE FIGURES

FIG. 1A illustrates a straw printed with a bar code, such as printed by a laser in accordance with certain embodiments described herein.

FIG. 1B illustrates a straw printed with a two-dimensional bar code in accordance with certain embodiments described herein.

FIG. 2A illustrates a top view of a cane marked with a two-dimensional bar code.

FIG. 2B illustrates a front view of a cane holding goblets marked with two-dimensional bar codes.

FIG. 2C illustrates a back view of a cane marked with two-dimensional bar codes.

FIG. 3 illustrates a straw marked with a laser.

FIG. 4 illustrates a sectional view of a marked straw.

FIG. 12 illustrates a color wheel indicating complimentary primary and secondary colors.

FIG. 13 illustrates a diagram relating to embodiments described herein.

FIG. 14 illustrates a diagram relating to embodiments described herein.

Figure 5A:
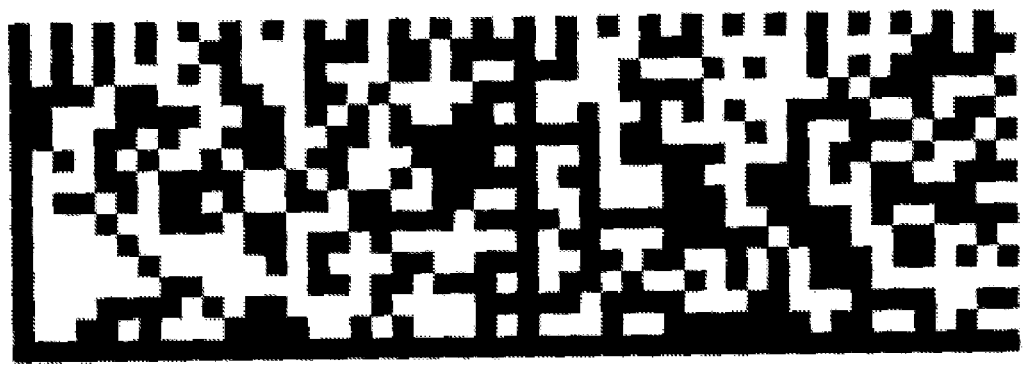
FIG. 5A illustrates a two-dimensional bar code in accordance with certain embodiments described herein.

While the present invention may be embodied with various modifications and alternative forms, specific embodiments are illustrated in the figures and described herein by way of illustrative examples. It should be understood the figures and detailed descriptions are not intended to limit the scope of the invention to the particular form disclosed, but that all modifications, alternatives, and equivalents falling within the spirit and scope of the claims are intended to be covered.

MODES FOR CARRYING OUT THE INVENTION

Turning now to FIG. 1A, a container (10) is illustrated as a straw (18), which may be a 0.25 ml French straw having a length L of about 133 mm and a diameter D of about 2 mm. Other containers are contemplated for use in certain embodiments as well. For example, the container (10) may be a different sized straw (such as a 0.5 ml straw), a goblet, a cane, a vial, a tube, a collection tube, an embryo tube, or containers which directly hold reproductive cells as well as other intermediate containers for holding groups of straws, tubes or vials. A limited printing area (12) is illustrated on one side of the straw (18), as a space that extends a length f, which extends nearly the entire length L of the straw (18). The length f and height h of the limited printing area (12) are indicated on FIG. 1A. However, the plane of the limited printing area (12) may have a greater height than depicted because it is wrapped around the curved cylindrical surface of the straw. The limited printing area (12) may extend about between about ⅕ the circumference of the straw and about 4/15 the circumference of the straw. As one example, the limited printing area (12) may extend about ¼ the circumference of the straw.

Within the limited printing area (12), various regulations provide required identifying information in alphanumeric print (20), which usually includes an International Bull Code (22), illustrated as "U001," followed by the registered bull name (24), illustrated as "REGISTERED BULL NAME." A registered bull number (26) "USA12345678" followed by the date (28) "101412" and NAAB code (30) "000HO12345" encompass the remaining required information on a straw (18). Collectively, this identifying information may also be referred to as the required information. Additionally, a linear bar code (14) is illustrated in the remaining portion of the limited printing area (12). Because the diameter of 0.25 ml straw is about 2 mm, the required printed material often takes a large portion of the limited printing area (12). Smaller fonts or smaller letter heights quickly approach unreadable sizes. The linear bar code (14) provides a means to reduce transcription errors and promote inventory tracking accuracy, but it is not necessarily a more compact means for printing information. For this reason, linear bar codes (14) may be limited to sizes which encode (17) characters or so.

FIG. 1B illustrates a straw (18) having the same limited printing area (12), as FIG. 1A. FIG. 1B illustrates the same required information (20) as FIG. 1A, including an International Bull Code (22) "U001," followed by the registered bull name (24); "REGISTERED BULL NAME," registered bull number (26) "USA12345678," as well as a date (28) "101412," and NAAB code (30) "000HO12345."

In the remaining limited printing area (12), a two-dimensional bar code (16) is printed. The two-dimensional bar code (16) may comprise a 48 by 16 matrix resembling checkerboard boxes that encode about 57 characters. In another embodiment, the two-dimensional bar code comprises a 32 by 96 matrix encoding additional characters. As one example, the two-dimensional bar code may include up to 104 or even up to 229 characters. In another embodiment, a less complex two-dimensional bar code may be used to encode 30 characters. In one embodiment, a Wide DataMatrix 2D barcode can be employed having a planar area of about 1.56 mm×3.51 mm representing 57 characters may be applied over the curved surface of a 0.25 ml straw having a diameter of about 2 mm. In another embodiment, a wide data matrix may be used which encodes 32 characters which are rapidly and repeatably readable by a reader. It can be appreciated, that larger two-dimensional barcodes may be applied on larger straws (18), such as 0.5 ml straws. The dimensions of the barcode may be varied to accommodate different sized straws. For example, the height of a two-dimensional bar code storing 32 characters may range between about 1.25 mm and about 1.75 mm on a straw. The width of a two-dimensional bar code storing 32 characters may range between about 2.5 mm and about 4.5 mm on a straw. In one embodiment, as many as 229 characters can be stored in a 48 by 48 data matrix etched on a 0.25 ml French straw. The availability of additional characters allows more information to be placed in on the straw in a scannable format. As one example, the two-dimensional bar code can contain all the required information in a scannable form. In another embodiment, the two-dimensional bar code can include a serial number in addition to a web address. The serial number may provide a cross reference index for accessing information regarding the straw (18) as well as information regarding the bull, collection, and processing.

Referring now to FIG. 2A, a top view of another container (10) in the form of a cane (34) is illustrated with a two-dimensional bar code (16). In FIG. 2B, a front view illustrates additional containers (10) suitable for storing reproductive cells in the form of goblets (36) holding straws (18). A two-dimensional bar code (16) may be ink printed or laser etched on the goblet (36) and the cane (34), to enhance data management and inventory tracking of reproductive cells, such as sperm, oocytes, or embryos that may be stored in straws (18). FIG. 2C, illustrates a back view of the cane (34), where two-dimensional bar codes are included at each goblet location. Each of the illustrated two-dimensional bar codes (16) may be encoded with identical information relating to the bull and freeze date, or they may contain a specific reference to which straws (18) in those goblets (36) are associated.

FIG. 3 illustrates a container (10) being marked by a laser (60). The container (10) may be a thin curved polymeric member, in the form of a straw (18). The straw (18), or thin curved polymeric member, may be characterized as an axial body (40) having an axial passage (42). While the axial body (40) and the axial passage (42) are illustrated as cylindrical tube, axial bodies may be produced with elliptical or polygonal cross sections as well. A 0.25 ml straw may have a length of about 133 mm and a diameter of about 2 mm, but straws (18) with varied dimensions may also be employed with certain embodiments described herein. With reference to FIG. 4, a sectional view is taken at AA, illustrating an axial body (40) with an exterior surface (48) and an interior surface (50) separated by a thickness (52). Straws (18) which are used in storing sperm, are often extremely thin to facilitate faster freezing and may have thicknesses between about 0.1 mm and 0.3 mm. It may be difficult to laser etch such a thin material in a manner that leaves visible marks and in a manner which allows the axial body to remain impermeable to fluids and unwarped.

An exemplary laser (60) for this purpose may be the 532 nm (green) laser in the Laser Marking System U-5G, available from RMI (Lafayette, Colo.). With the appropriate focusing lens a beam spot (62) between about 40 µm and 80 µm may be generated. Additionally, a modification available from RMI incorporating a beam expander and wave plate allows the generation of smaller beam spots as small as about 25 µm. Settings for the laser power, step size, speed, pulses, and number of passes may then be set to form a visible mark (64) on the exterior surface (48) of the straw (18). A great deal of difficulty exists in producing any mark on the straw, the ability to print a two-dimensional bar code (16), with enough resolution to be read by a scanner is an evasive proposal, and is compounded by previously discussed issues regarding extremely thin wall thicknesses and the need retain fluids. The beam spot (62) of the laser (60) may be directed to a plurality of pixel locations (68) on a marking plane (70) of the straw (18) to produce a visible mark (64) in the form a two-dimensional bar code (16). The marking plane (70), may substantially overlap the limited printing area (12), or may occupy a portion of the limited printing area (12). In one embodiment, the step size, laser power, beam spot size, pulse frequency, and number of passes are configured for producing char marks on a straw which are roughly circular in shape and which measure about 15 microns in diameter. Such an arrangement, allows for single units within the data matrix to be produced by four char marks in a 30 micron by 30 micron area. In this manner, a 48 by 48 data matrix (encoding 229 characters) is able to fit on the side of a 0.25 ml French straw with good resolution. However, to improve scanning time or reduce the optical requirements of scanners, larger two-dimensional bar codes with fewer units may also be used.

After marking, the straw (18) may be filled with sperm or other reproductive cells in known manners. As but one example, a machine like that described in International Patent Application WO/2008/031793 may be employed, and the entire content of that application is incorporated herein by reference. After, or during filling, one or more plugs (66) may be employed at a first body end (44) and a second body end (46).

Figure 6:
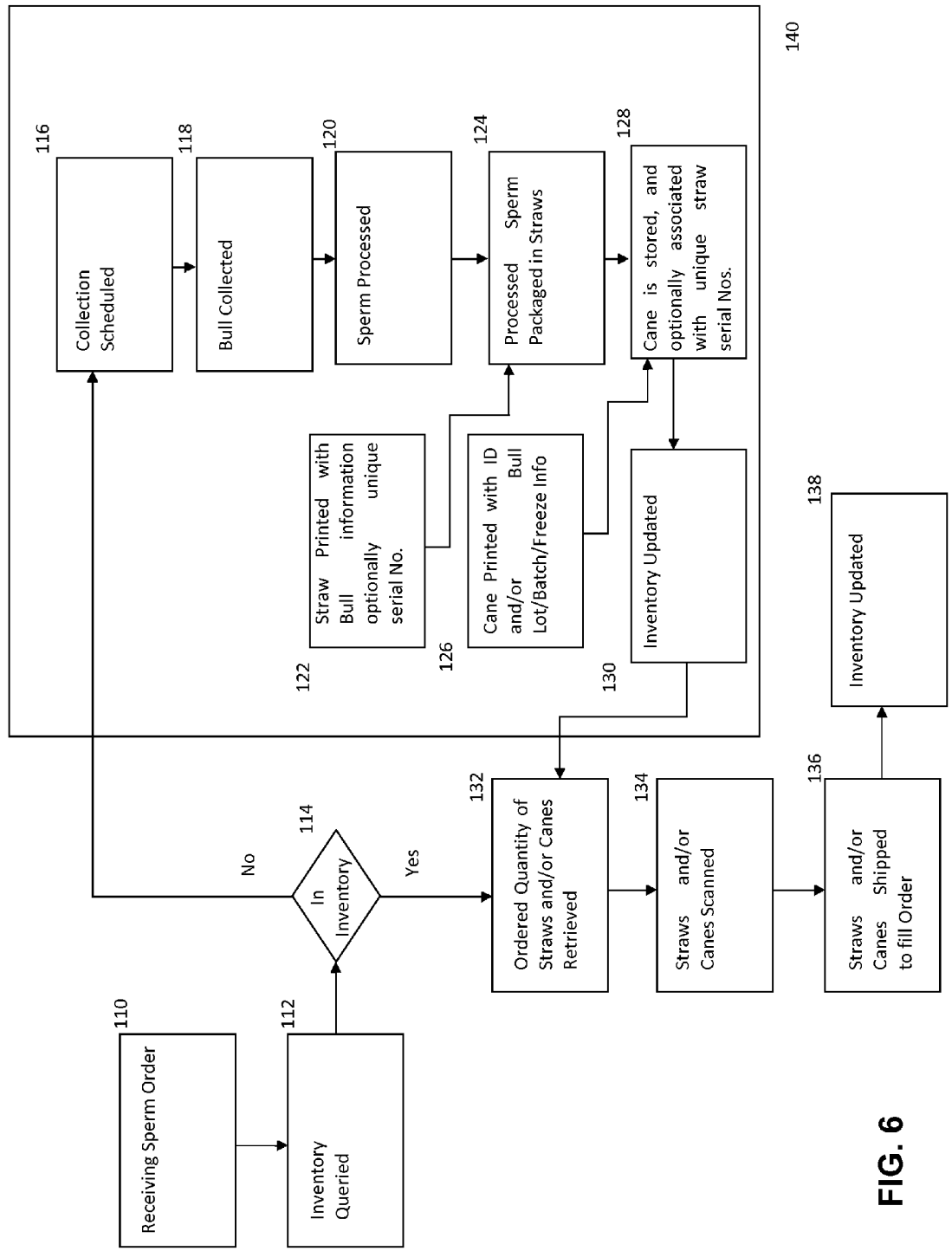
FIG. 6 illustrates a flow diagram in accordance with certain embodiments described herein.

Turning to FIG. 6, an example of a method which may be facilitated by the incorporation of two-dimensional bar codes onto straws begins with the step of receiving a sperm order (110). The sperm order may be received, through a catalogue, online, or through an intermediary and the order may be for sperm from a particular identified source, such as a bull. Regardless of the manner in which the order is received, the order, or a corresponding order is placed with a processing facility maintaining processed sperm in inventory. Once the order is received the inventory may be queried (112). The inventory is queried for the appropriate quantity of straws for the identified source, or the desired bull. Additionally, the order and the query may provide further specifics, such as X or Y chromosome bearing sperm or particular volume straws, such as 0.25 ml or 0.5 ml. At the time of the query, a determination (114) is made as to whether the quantity of straws ordered are in stock. In the event the inventory is lacking the requested quantity of items, the production process (140) may be initiated to fill the order.

In the production process (140), a collection schedule may be generated (116) reflecting collections from a plurality of bulls, or other animals, including the source of sperm related to the order. The collection schedule (116) may reflect resource allocation for further sperm processing and may represent a modification to a routine collection schedule. According to the schedule, the bull presenting the source of sperm may be collected (118). The production process (140) may run independent from any one order and bulls may be collected on regular schedules. At step (120), collected bull sperm may be processed. Sperm processing (120) may include, extending sperm to a specified concentration, freezing sperm, sex sorting sperm, bulk sorting sperm, or checking sperm motility, or any combination thereof.

Straws may be printed at step (122) with the required bull information for the collected bull. Straws may be printed with all the required information previously described and may incorporate a laser etched two-dimensional bar code to improve the quantity of scannable data readily available for storage and inventory purposes. In one embodiment, each straw may be encoded with a unique serial number. In one embodiment, required bull information is reprinted in the form of a two-dimensional bar code by a laser printing process. In another embodiment, the unique serial number is encoded in the bar code. A two-dimensional bar code may additionally be encoded with bull information and with a reference to an index for the serial number, such as a web address. As described above, a two-dimensional bar code may be incorporated to increase the number of characters available. In another embodiment, groups of straws are encoded with a lot or batch number which provides some reference to the specific bull collections or freeze lots, even in the event processed sperm originates from multiple collections. The processed sperm may be packed into the marked straws (124).

Whereas previously straws may have been grouped in goblets placed into a cane that only identifies the bull, the current method provides canes imprinted with additional identifying information. The additional identifying information may be in the form of a scannable bar code to help track inventory, such as a two-dimensional bar code. In addition to the bull name, the cane may be provided with a cane identification number. Freeze date/batch/lot and other particulars may be associated with the cane identification number in a data base (126). The two-dimensional bar code provides a means for including additional information in the limited space of the cane, and the identification number allows specific tracking information beyond merely the bull identification. In one embodiment, specific straw serial numbers may be associated with a cane identification number (128). In another embodiment, canes are labeled with processing information, such as the freeze date. Because some canes may accommodate more than one goblet, in one embodiment, each goblet may also be encoded with a scannable bar code containing identifying information. The information imprinted on the bar code may be a serial number, but may also contain bull specific information or information about the lot, batch or freeze date. Each cane and/or goblet may be scanned, or the inventory may otherwise be updated (130) to reflect the addition of a current batch of straws, ending an iteration of the production process (140).

Returning to the decision tree (114), the process may continue with the step of retrieving the appropriate number of canes and/or straws (132) to fill the order. Because each cane is associated with more detailed information regarding the specific straws contain therein, orders may be filled by retrieving an appropriate number of specified canes. Depending on the size of the order, entire canes may then be scanned for filling (134) the order and the appropriate corresponding number of straws may be taken out of inventory. Individual straws may be pulled out of canes to finish the proper quantities. Those canes from which straws have been removed, may be updated in the database to reflect the current number of straws they hold. The straws and/or canes may then be shipped (136) to fill the order and the electronic inventory is updated (138) to reflect the quantity shipped.

Figure 7:
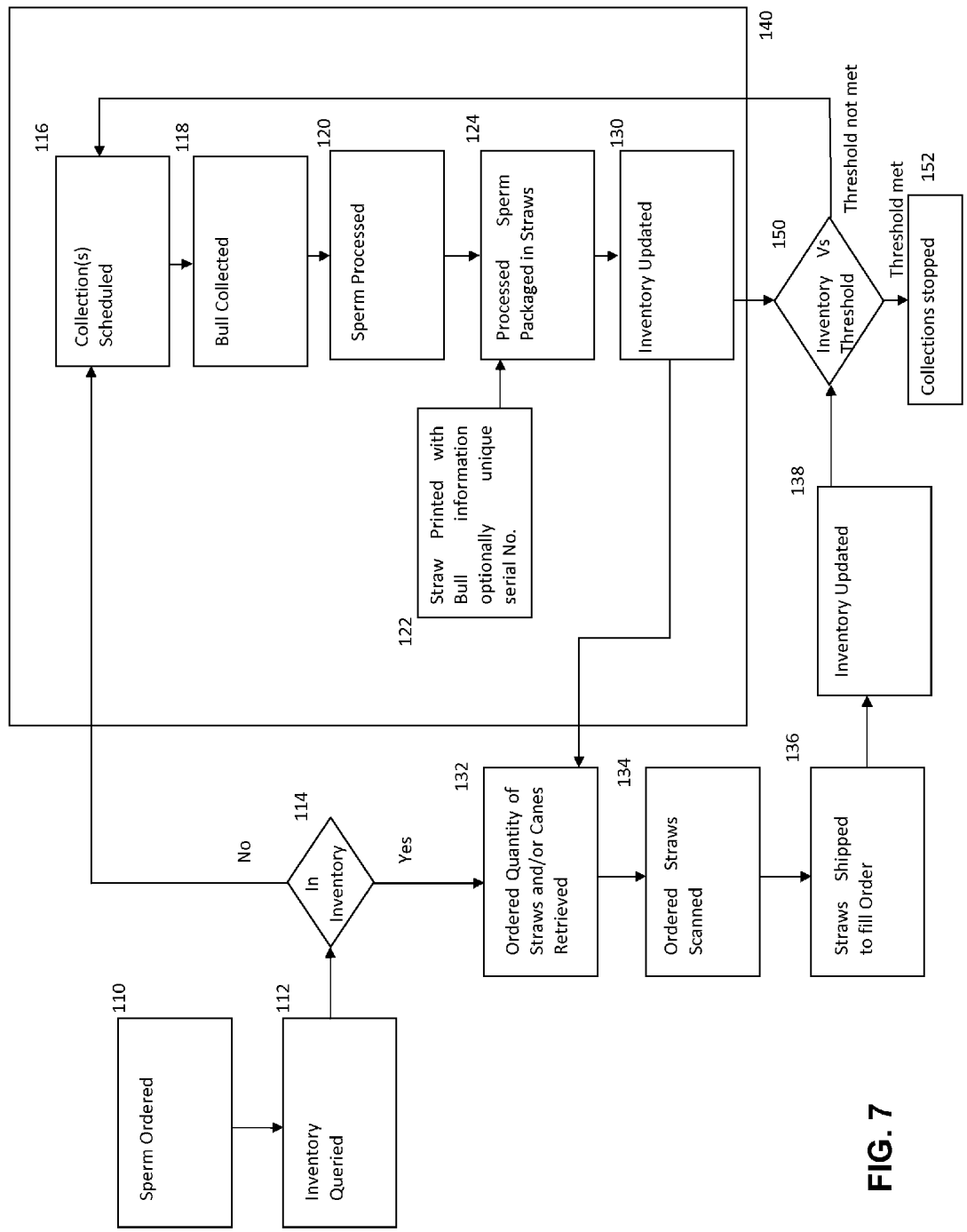
FIG. 7 illustrates a flow diagram in accordance with certain embodiments described herein.

An alternative, but similar, embodiment illustrated in FIG. 7, provides for an inventory check versus a threshold (150). The inventory check may be performed on a regular basis, or it may be automated each time the inventory is updated with new inventory (130) and/or each time inventory updated for shipments sent out (148). In either event, in the case where the threshold is not met for a particular bull, that bull may be entered into a collection schedule (116). The threshold may be obtained from historical data for a particular bull. As an example, the threshold may be modified when the current demand for a specific bull is high. The threshold may also be modified by seasonal factors, such as seasonal changes in demand and seasonal changes in the fertility. The threshold may encompass a range having a minimum and a maximum. In the event an upper threshold is exceeded, collections on that bull may be stopped (152).

In an alternative embodiment, a bull may already be on a collection schedule, such as being collected once a week. In the event the inventory drops below a threshold minimum the collection schedule may be increased. In the event that the inventory for that bull goes above a maximum threshold, the schedule may be reduced or stopped.

Figure 8:
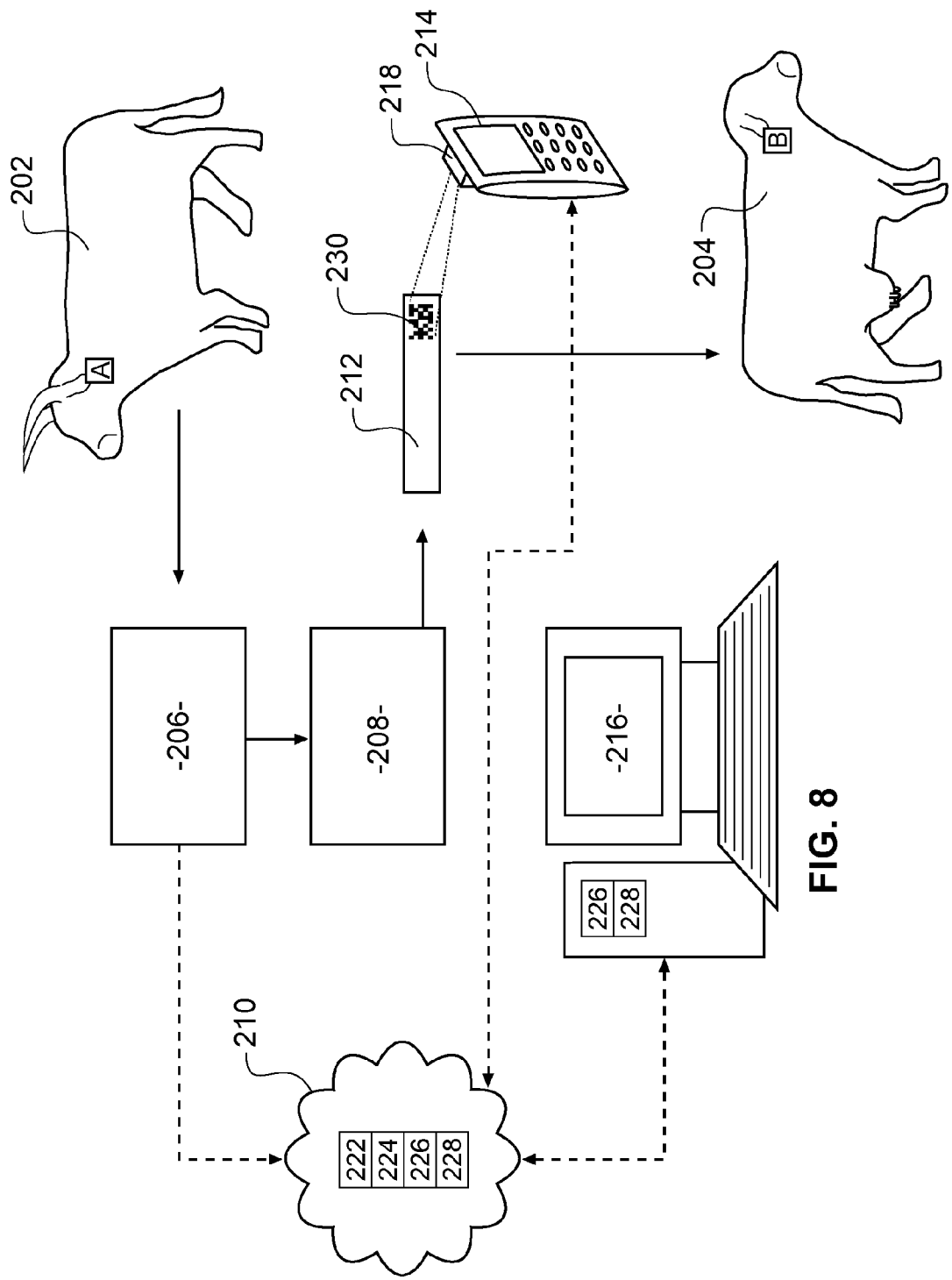
FIG. 8 illustrates a flow diagram in accordance with certain embodiments described herein.

Turning now to FIG. 8, a method is illustrated where a sperm sample is collected from an identified source (202), for example a registered bull. The sperm sample may be associated with the identified source (202). A processing step (206), may include any of: extending sperm to a desired concentration, staining sperm, sorting sperm, and freezing sperm. Identifying batch, freeze, lot or other processing information, such as quality control or sperm motility, may be generated in association with these processing steps (206). At step (208), the sperm sample may be inventoried and stored in straws (212) which have been marked with two-dimensional bar codes (230). It should be appreciated there may be some temporal overlap between those actions described at (206) and (208). For example, the step of freezing will occur after sperm is packed into marked straws. In one embodiment, the two-dimensional bar code (230) provides encoded information in the form of bull information, while in another embodiment, the encoded information provides a serial number, or other cross referenced information.

The marked straws (212) containing sperm from the identified source (202) may be shipped out to an end user for insemination in an intended recipient (204). Prior to insemination, the bar code (230) of the marked straw (212) may be read with a portable device (214). Commercially available devices may be suitable with an upgraded magnification lens (218), or purpose build portable devices could also be used. Suitable portable devices (214) may include an Ipad (Available from Apple Inc, Cupertino, Calif., USA), as well as other tablets, cell phones having cameras, or other portable image based scanners, so long as an appropriate magnification lens can be incorporated. Reading the bar code (230) may be for the purpose of verification to ensure sperm from the identified source (202) is being inseminated into the intended recipient (204). The bar code (230) may also be read to more accurately transcribe fertility data (226) and quality control data (228). For example, the two-dimensional bar code may be read to begin compiling a database of calf information beginning the parentage and lineage of any potential calf. Additionally, a great deal of quality control and fertility data may be managed from such a platform. For example, in one embodiment, the two-dimensional bar code provides a reference number, or serial number, (222) which permits online access to additional information about the freeze lot (224) from which the straw (212) came. The additional information can include specific processing information, like the motility and morphology of that collection. Additional bull information could also be available, such as a picture of the bull, information about the bull collection, information about the bull farm, information about the site the sperm was processed and the like. The individual performing AI may also be recorded so that bull fertility may be tracked against any number of variables when the information is combined. For example, across thousands of straws, data may be organized demonstrating the fertility of a particular bull, the fertility sperm processed from a particular bull on a particular date, and the like. This data may be transferred from the portable device (214) to a personal computer (216), or the portable device (214) may directly access the internet (210). In either event, the bar code may contain encoded information including a serial number (222) which is unique to the straw (212), or reference to the batch, lot, or freeze date of the straw (212).

Methods of Laser Printing on a Straw

Straws, such as 0.25 ml straws and 0.5 ml straws, used to transport and store biological products, biological materials, biological fluids, embryos, inseminate for the artificial insemination of an animal, semen, ova, or the like may particularly benefit from the methodologies incorporating two-dimensional bar codes previously described.

However, the resolution of ink jet printers is insufficient based on the space requirements of marking planes on conventional 0.25 ml straws in particular. Currently, printing on conventional cylindrical artificial insemination straws typically involves a mechanical system that accepts individual straws from a hopper containing a plurality of straws, and passes the straws length wise proximate the printer head of a stationary ink jet printer. The printer head disperses ink droplets at appropriate volumes, trajectories and times to produce marks on one side along the length of the straw. This approach can produce visible marks with respect to the background color of the straw to assist in identification of the content of each straw. Marks typically applied to the straws which, for example, contain inseminates for artificial insemination provide characters which can identify the source of the semen, animal name, date, company information, freeze lot, and sex-selection characteristics such as being enriched for X-chromosome bearing sperm or Y chromosome bearing sperm, or the like.

However, there are substantial unresolved problems associated with marking straws with an ink-jet printer and with the resulting ink marks. One substantial problem with marking straws by ink jet printer is that characters may not be sufficiently small and of sufficiently resolved to include all the necessary or desired information on the imprintable area of the straw. This problem may be exacerbated due to international trade requirements which now necessitate additional information on individual straws. Additionally, small variations in the speed at which straws pass the ink jet printer head can result in mark distortions such as compressed, stretched, or variable contrast marks. Specifically, the resolution required to produce a readable two-dimensional bar code containing any desirable number of characters is not achievable with conventional straw printing methodologies.

Figure 9:
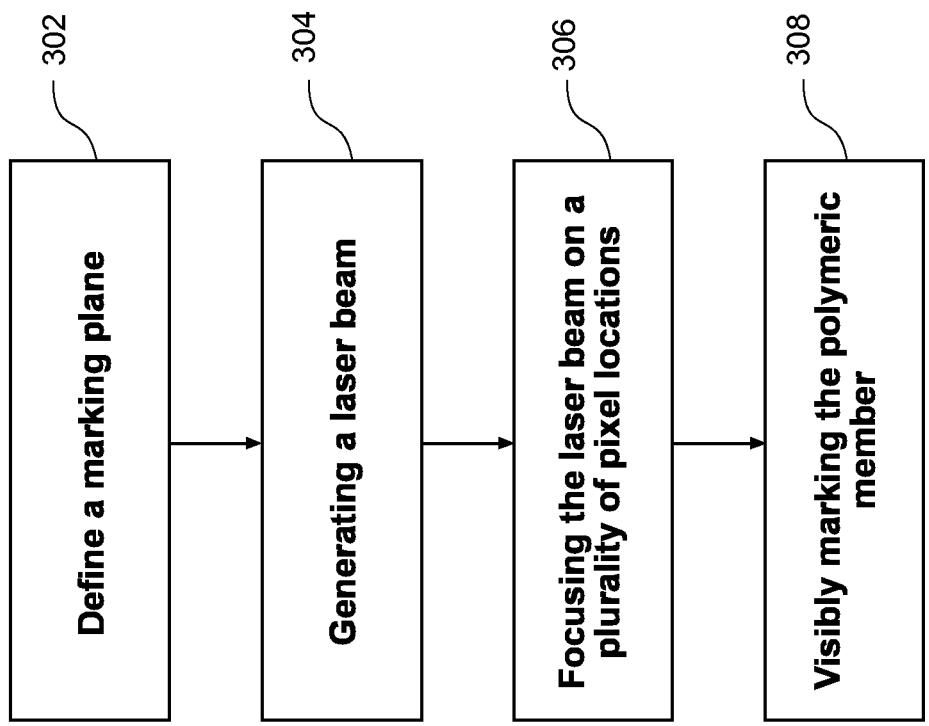
FIG. 9 illustrates a block diagram relating to methods described herein.

Referring to FIG. 9, a general method is illustrated (300) for achieving laser etched marks on a straw, and particular for achieving laser etched marks with sufficient resolution to produce a barcode in the form of a two-dimensional matrix. The method may begin at step (302) with defining a marking plane. The marking plane may be defined on a thin curved surface, such as a polymeric member having an axial body defining an axial passage communicating between a pair of body ends. As one example, the marking plane may be the exterior surface of a cylindrical vessel and as another example, the marking plane may be the exterior surface of a 0.25 ml or 0.5 ml straw. The step of defining a marking plane may be performed by the execution of written computer instructions and may be done alone, or in combination with user input. Using a computer multiple marking planes may be defined on plurality of straws for sequential marking.

At step (304) a laser beam is generated, such as by any of the lasers sources previously described. In some embodiments, it may be desirable to select a laser source with particular characteristics to facilitate producing visible marks on thin, curved surfaces. As one example, a wavelength, or other operational characteristic, of the laser source may be coordinated with a color of the straws being marked. In such an embodiment, the polymeric member may contain an additive, such as a colorant, or dye, which may be doped into the polymeric matrix of the polymeric member. The colorant may have electromagnetic radiation absorbance properties, such as local or absolute maxima in the absorption spectra. The local or absolute maxima of the absorption spectra may be in the ultra violet or visible light wavelength ranges. For example, the local or absolute maxima of the absorbance spectra may be in the range of about 250-400 nm, or in the range of about 400 nm-700 nm. The local or absolute maxima of the absorbance spectra may also be matched or loosely matched to particular wavelengths of specified lasers, such as about 266 nm, 355 nm, 435 nm, 460 nm, 532 nm, 555 nm, or 570 nm. In one embodiment, the laser source may comprise a laser source operating at a wavelength of 355 nm and the colorant having a local maximum in the absorbance spectra between about 300 nm and 380 nm.

As another example, the fluence, irradiation dwell period, and/or step size may be adjusted based on the material being marked or based on the color of the curved surface. Conversely, it may be desirable to select straw colors based upon the laser source to be used. In some embodiments, straws may be doped with photochromatic dyes. Alternatively, only the portions of the straws comprising the marking plane may be doped with photochromatic dyes. A laser operating at the ultra violet wavelength may be used for directly marking on such straws doped with photochromatic dyes.

In another embodiment, straws may be doped with a photochromatic dye providing the straws with an active state and an inactive state. An arc lamp, ultra violet light source, or other light source generally containing light at the ultra violet frequency may be used to shift straws from the inactive state to an active state. Straws in the active state may exhibit different color properties and different laser absorbance properties as compared to their inactive state.

At step (306) the laser beam may be focused on a plurality of pixel locations on the marking plane or multiple marking planes. The step size and irradiation dwell period may be adjusted in a computer based upon the surface to be marked, the material to be marked, the color of the material to be marked, or the activated color of the material to be marked when activated. Such adjustments may be made for the purpose of visibly marking a surface without causing the deformation of the member and without the surface becoming permeable.

At step (308) a visible mark (18) may be produced on the surface of the polymeric member. The polymeric member may remain undeformed and impermeable after such marking.

Impedance Matching

Figure 10:
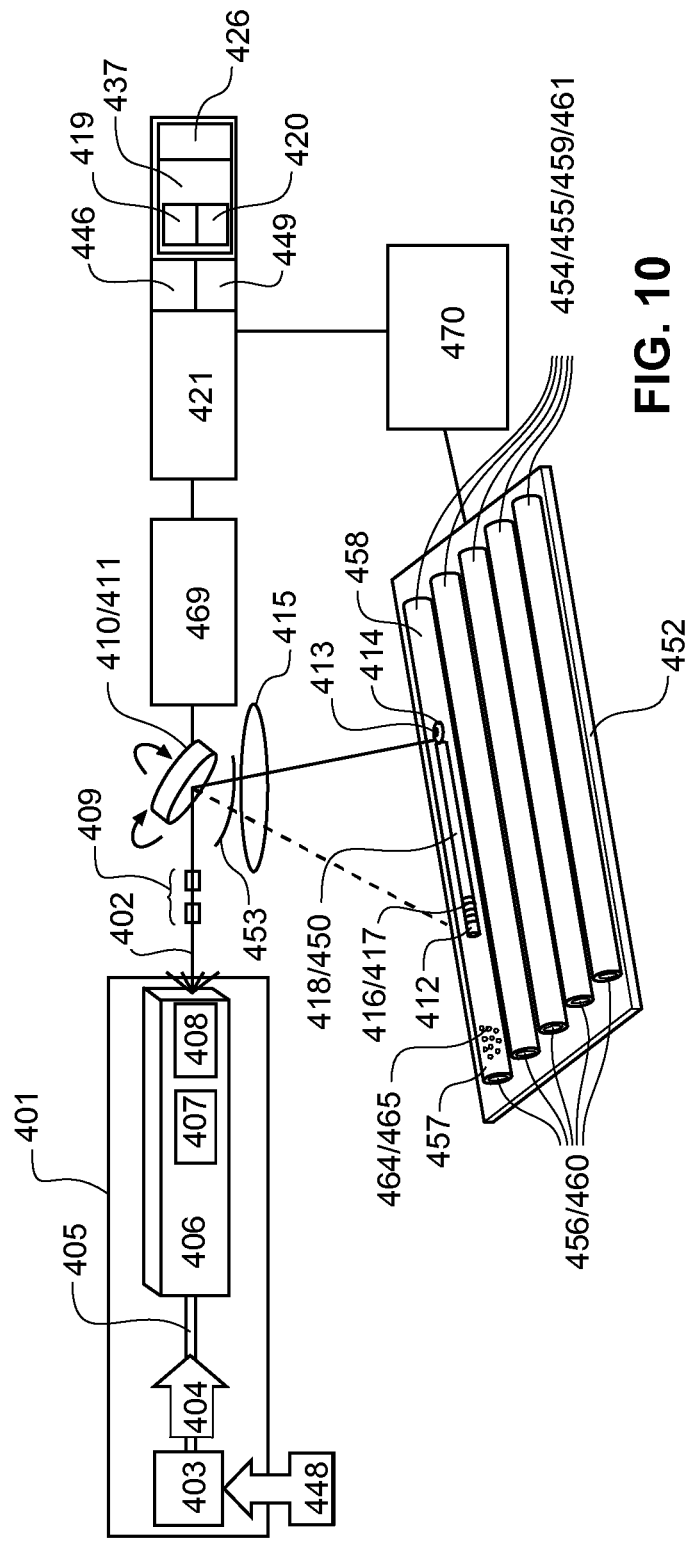
FIG. 10 illustrates a diagram relating to embodiments described herein.

Now referring primarily to FIG. 10, a laser source (401) that operates to generate a laser beam (402) is illustrated. A non-limiting example of a laser source (401) may include a laser diode (403), which generates laser light (404) that travels within a fiber optic cable (405) to a laser head (406). At a fixed voltage, amperage (448) to the laser diode (403) may be adjusted to provide a laser beam (402) adjustably variable within a power range. The laser head (406) may contain a laser crystal (407) and a Q-switch (408). As a non-limiting example, the laser crystal (407) may be a vanadate (Nd:YVO4) laser crystal (407), which absorbs laser light (404) at 808 nanometers ("nm") from the laser diode (403) and produces a continuous waveform laser light (404) at a wavelength of 1064 nm. The Q-switch (408) acts to convert the continuous waveform laser light (404) from the laser crystal (407) (such as the vanadate crystal) to serial laser beam pulses (409). The Q-switch (408) may be opened and closed in the range of about 1,000 to about 70,000 times per second. While the Q-switch (408) is open, the stored energy of the laser crystal (407) emits a laser beam (402) until the Q-switch (408) closes resulting in a laser beam pulse (409). The duration of the laser beam pulse (409) may be adjusted by a change in the switch rate of the Q-switch (408). It is not intended that the above example of a laser source (401) be limiting with respect to the numerous and wide variety of laser sources (401) which may be utilized to produce a laser beam (402) (whether continuous or pulsed) having a correspondingly wide range of waveform characteristics such as frequency or amplitude or both that may be suitable for use with particular embodiments described herein. In particular, non-limiting examples of suitable laser sources (401) include Nd:YVO or YAG lasers (wavelength 1064 nm), frequency-doubled Nd:YVO or YAG lasers (wavelength 532 nm) and Excimer lasers (wavelength 193 nm 351 nm).

The laser beam (402) emitted from the laser head (406), whether continuous or pulsed, may be received by one or a pair of scanning mirrors (410) (411), which may be collectively referred to as a steering element. The pair of scanning mirrors (410) (411) can be positioned to direct the laser beam (402) or each of the laser beam pulses (409) incident upon a marking plane (412). Alternatively, acousto-optical modulators and other refractive and reflective elements could be used to steer the laser beam (402). The laser beam (402) may also be optically focused to produce a laser beam spot (413) having a boundary (414) of fixed dimension on the marking plane (412) by passing the laser beam (402), or each of the laser beam pulses (409), through a focusing lens (415), such as an F-Theta lens. By optically focusing the laser beam (402) through the focusing lens (415) the boundary (414) of the laser beam spot (413) can be adjusted to a diameter in the range of about 20 microns to about 100 microns. Particular embodiments provide a laser beam spot (413) incident upon the marking plane (412) with a diameter of about 40 microns. In one embodiment, modifications such as beam expanders and wave plates may be incorporated in the laser head (406) to provide a beam spot of about 25 microns or less having a more uniform beam intensity profile. Such modifications may permit uniform marking in the form of chars roughly 15 microns in diameter. If the power of the laser beam (402) is fixed, the lesser the dimension of the laser beam spot (413) the greater the fluence of each of the laser beam pulses (409) incident upon the marking plane (412).

A plurality of pixels (416) may each be assigned to a corresponding plurality of pixel locations (417) in relation to the marking plane (412). The plurality of pixel locations (417) may correspond to a marking pattern (450) containing information in the form or text, barcodes, logos, trademarks, or other representations of information. The laser beam spot (413) may be centered over one or more of the plurality of pixels (416) by operation of the pair of scanning mirrors (410)(411). The step size, or spacing between the plurality of pixels (416), can be adjusted to increase or decrease the distance between any two of the plurality of pixel locations (417). If, for example, the laser beam spot (413) has a diameter of about 40 microns and the distance between any two of the plurality of pixels (416) is about 30 microns, serial centered incidence of the laser beam (402) on any two of the plurality of pixels (416) will result in overlapping incidence of the laser beam (402) on the marking plane (412). If the laser beam spot (413) has a diameter of about 40 microns and the distance between any two of the pixel locations (417) is about 50 microns, then serial centered incidence of the laser beam (402) on any two of the plurality of pixels (416) will result in spaced incidence of the laser beam (402) on the marking plane (412). Understandably, a lesser diameter laser beam spot (413) and a lesser distance between the plurality of pixel locations (417) can increase the resolution of a resulting visible mark (418) on the marking plane (412), but can also increase the marking period (419) in which to complete marking of the visible mark (418).

As to each of the plurality of pixel locations (417) an irradiation dwell period (420) can be adjusted to increase or decrease the amount of time the laser beam (402) dwells at each of the plurality of pixel locations (417). As a non-limiting example, a relatively low fluence of the laser beam (402) may necessitate a longer irradiation dwell period (420) at each of the plurality of pixel locations (417) to achieve the same result as compared to a relatively high fluence at each of the same plurality of pixel locations (417) acting on the same marking plane (412). The irradiation dwell period (420) may also be adjusted to encompass the duration of one laser beam pulse (409) or the duration of a plurality of laser beam pulses (409) at the same one of the plurality of pixel locations (417).

The term visible, may be interpreted as visible by the naked eye, as well as by machine vision approaches, since at some stage the straws may be 'read' by a device that is computer-based or has aspects of artificial intelligence that mimic human functions. Similarly, the term visible markings (418) may include laser etched markings, such as divots, wells, charring, or other localized modifications of the surface depth or color of the surface being marked which are visible to the naked eye or to machine vision approaches.

Producing visible markings (418) in a desired marking pattern (450) requires coordination of a variety of factors. One or more than one laser source (401), may produce laser beam pulses (409) at a coordinated rate, if pulsed, and may have a coordinated fluence incident upon the marking plane (412) that can be adjusted by varying laser beam power and/or the boundary (414) of the laser beam spot (413). The positioning of the pair of scanning mirrors (410)(411), or alternatively beam light positioners, to direct the laser beam (402) incident upon the marking plane (412) may be coordinated to control spacing between a plurality of pixel locations (417), as well as the irradiation dwell period (420) of the laser beam (402) incident upon each of the plurality of pixels (416). The scanning mirrors (410)(411), or another laser beam positioning mechanism, may be replaced by, or used in conjunction with a carrier (452) movable relative to the laser beam (402). For example, the carrier (452) may be coordinated with a carrier position controller (470) for movement in the longitudinal direction, while the scanning mirrors (410)(411) can direct the laser beam (402) orthogonally.

Coordination of the above-described factors can be controlled by a computer (421) having a processing unit (426), a memory element (437), and a bus which operably couples components of the computer (421), including without limitation the memory element to the processing unit. The computer may be a conventional computer such as a personal computer or a lap top computer; however the invention is not so limited. The processing unit may comprise one central-processing unit (CPU), or a plurality of processing units that operate in parallel to process digital information.

One or more laser control units (446) may be in communication with the laser (401) and controlled by the computer (421). Execution of the instructions by the processing unit (426) causes the laser control unit (446) to perform steps to generate laser control signals for operation of the laser source (401) including the laser diode (403), amperage (448) to the laser diode (403) and any switch such as the Q-switch (408) to generate laser beam pulses (409).

The marking modules provide a sequence of instructions executed by the processing unit (426). Execution of the instructions by the processing unit (426) causes the marking control unit (449) to mark, in serial order, each of a plurality of pixels (416) at plurality of pixel locations (417) corresponding to the marking pattern (450), which may be input by the computer user. Execution of the instructions may produce a marking control signal for steering the pair of mirrors (410)(411) with a steering controller (469) to direct the laser beam (402) to each of the plurality of pixels (416) at each of the corresponding pixel locations (417) on the marking plane (412) for an assigned irradiation dwell period (420) according to the marking pattern (450). In certain embodiments, execution of additional instructions may produce a marking control signal for operating a carrier position controller (470) to position a marking carriage (452). In certain embodiments the instructions may provide marking control signals for manipulating the marking carriage (452) to serially position multiple straws (461) within the travel range (453) of the laser beam (402).

Polymeric members (454) having thin and/or curved surfaces are illustrated on the marking carriage (452) undergoing laser etching. Particular embodiments of the polymeric members (454) have an axial body (455) which defines an axial passage (456) communicating between a pair of body ends (457)(458) including, but not limited to, cylindrical vessels (459) defining a cylindrical passage (460)(as shown in FIG. 3). As a non-limiting example, some embodiments relate to straws (461) manufactured for holding a variety of biological materials, and in certain embodiments, cryogenically frozen biological materials such as embryos, semen, ova, sperm cells, sex-selected sperm cells (subpopulations of sperm cells selected on the basis of being X-chromosome bearing or Y-chromosome bearing), sex-selected embryos, or the like. Straws (461), as a non-limiting example, can have a length of about 133 mm or about 280 mm with an outer diameter in the range of about 0.8 mm to about 5 mm and an inner diameter in the range of about 0.7 mm to about 4.9 mm and having in a wall thickness in the range of about 0.1 mm and about 0.2 mm.

Table 1 provides a non-limiting list of straws (461) suitable for use with particular embodiments of the invention, which can be obtained from IMV Technologies, 10, rue Clemenceau, 61300 L'Aigle, France, or other sources.

TABLE 1

| Straws | Color | Cat. No. |
| --- | --- | --- |
| 0.5 ml | clear | 5569 |
| 0.5 ml | red | 5702 |
| 0.5 ml | green | 5568 |
| 0.5 ml | purple | 5703 |
| 0.5 ml | yellow | 5707 |
| 0.5 ml | salmon | 5715 |
| 0.5 ml | putty colored | 5711 |
| 0.5 ml | pistachio | 5746 |
| 0.5 ml | pink | 5712 |

TABLE 1-continued

| Straws | Color | Cat. No. |
|---|---|---|
| 0.5 ml | pastel red | 5709 |
| 0.5 ml | pastel green | 5710 |
| 0.5 ml | pastel blue | 5697 |
| 0.5 ml | pastel grey | 5698 |
| 0.5 ml | pastel yellow | 5590 |
| 0.5 ml | pastel orange | 5685 |
| 0.25 ml | clear | 5565 |
| 0.25 ml | green | 5570 |
| 0.25 ml | purple | 5573 |
| 0.25 ml | yellow | 5578 |
| 0.25 ml | pink | 5581 |
| 0.25 ml | light blue | 5680 |
| 0.25 ml | salmon | 5582 |
| 0.25 ml | putty colored | 5585 |
| 0.25 ml | pastel red | 5567 |
| 0.25 ml | pastel blue | 5584 |
| 0.25 ml | pastel grey | 5577 |
| 0.25 ml | pastel yellow | 5575 |
| 0.25 ml | pastel orange | 5580 |
| 0.25 ml TBS | clear | 17011 |
| 0.25 ml TBS | pastel orange | 17017 |
| 0.25 ml TBS | pastel grey | 17015 |
| 0.25 ml TBS | pastel red | 17012 |
| 0.25 ml TBS | pastel pistachio | 18888 |
| 0.25 ml TBS | salmon | 19708 |
| 0.25 ml TBS | pink | 19707 |
| 0.25 ml TBS | white | 18299 |
| 0.25 ml TBS | pastel yellow | 17016 |
| 0.25 ml TBS | pastel green | 17013 |
| 0.25 ml TBS | pistachio | 19709 |
| 0.25 ml TBS | pastel blue | 17014 |
| 0.25 ml | white plug | 6937 |
| 0.25 ml | grey plug | 6939 |
| 0.25 ml | yellow plug | 6942 |
| 0.25 ml | red plug | 6941 |
| 0.25 ml | blue plug | 6940 |
| 0.25 ml | green plug | 6938 |

Embodiments of the polymeric members (454) including conventional artificial insemination straws (461) are formed from polyvinyl chloride ("PVC") and polyethylene terephthalate ("PETG"). Additives or dispersed colorants (464) such as carbon black, graphite, calcium silicates, zirconium silicates, zeolite, mica, kaolin, talc cordierite, and colorants such as organic pigments, inorganic pigments, photochromic dyes, or polymer-compatible organic dyes can be dispersed throughout the polymeric matrix (465) of the polymeric members (454). These polymers have been shown to be impermeable to a wide range of biological materials including impermeability to hepatitis B and HIV-1 virus and other viruses, or the like, even when the straws containing the biological materials are cryogenically frozen. Benifla, Jean-Louis et al., "*Safety of cryopreservation straws for human gametes or embryos: a preliminary study with human immunodeficiency virus 1*", Human Reproduction, Vol 15, No. 10, 2186-2189 (October 2000).

Figure 11:
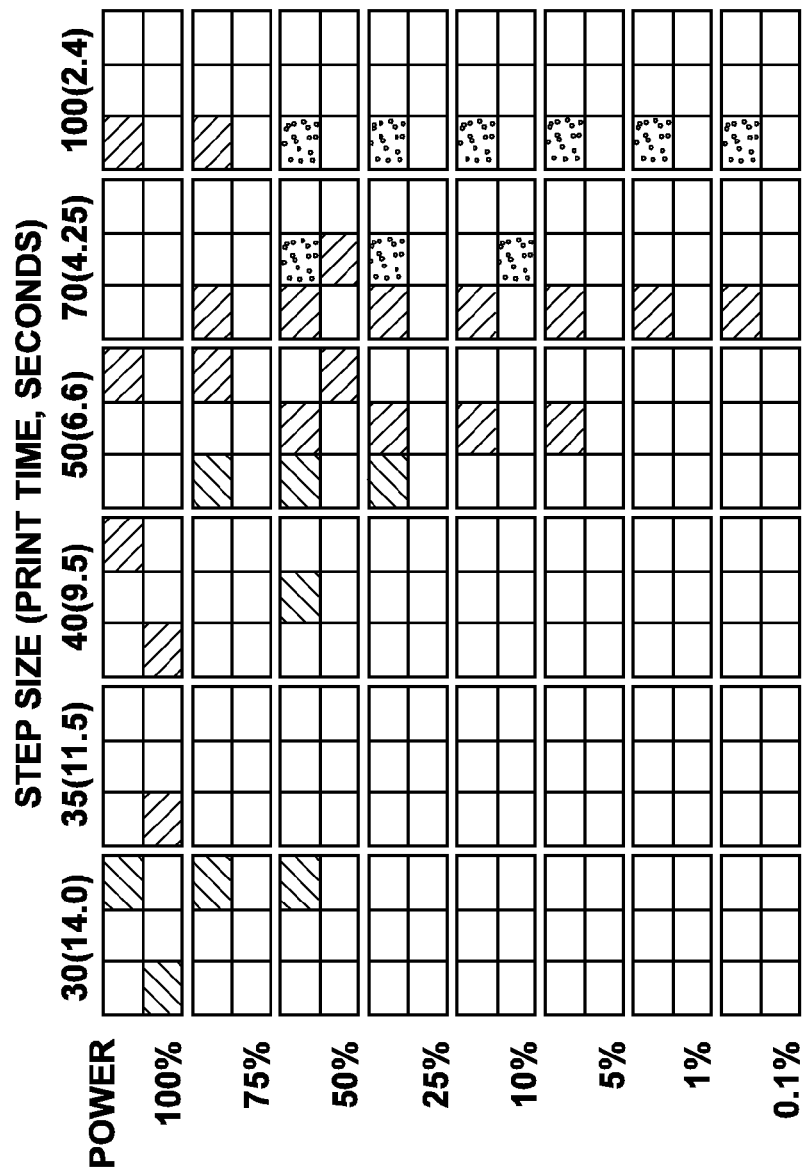
FIG. 11 illustrates the results of trials in which a plurality of polymeric members are each laser marked according to certain embodiments described herein.

FIG. 11 provides a tabular summary of the results obtained in trials in which a laser beam (402) was made incident upon a marking plane (412) of certain embodiments of a polymeric member (454) formed from a PVC polymer to provide a length of about 133 mm with an outer diameter of about 4 mm and an inner diameter in the range of about 3.8 mm resulting in a wall thickness of about 0.1 mm. Each trial was performed using a laser source (401), which included a vanadate (Nd:YVO4) laser crystal (407) that absorbs laser light (404) at 808 nanometers ("nm") from a laser diode (403) to produce a continuous waveform laser light (404) at a wavelength of 1064 nm, frequency-doubled to produce a laser beam (402) having a wavelength of 532 nm. The laser beam (402) was switched using a Q-switch (408) to generate laser beam pulses (409) having a frequency of 10 kHz. The boundary (414) of the laser beam (402) incident upon the marking plane (412) of each polymeric member (454) was fixed to establish a laser beam spot (413) having a diameter of about 40 µm. The fluence of each of the plurality of laser beam pulses (409) was controlled by adjusting the amperage (448) of the current delivered to the laser diode (403) to achieve a range of power adjustable between 0.1% and 100% of about 2 W. The step size, or distance between each of a plurality of pixel locations (416), was controlled by the marking module of the computer (421) to establish a range of distance between any two of a plurality of pixels (417) within a range of about 30 µm and about 100 µm. The plurality of pixel locations (416) established by the marking module of the computer (421) matched a marking pattern (450) constant between trials. The laser beam (402) was centered incident upon each of the plurality of pixels (16) included in the marking pattern (450) for a irradiation dwell period (420) controlled by the marking module to achieve a write time for the marking pattern (450) in a range of about 2.4 seconds and about 14 seconds.

Now referring primarily to FIG. 11, in accordance with the procedure above-described thirty-seven individual trials were conducted on a corresponding plurality of polymeric members (454) obtained from IMV Technologies, 10, rue Clemenceau, 61300 L'Aigle, France, having catalog number 5702 (Red) (see key in FIG. 11 upper left hand corner of each data grid). Fluence of laser beam pulses (409) was adjusted between 0.1% and 100% of 2 W and the step size was adjusted between about 50 µm and about 100 µm as above described to generate various laser marking conditions. All other laser marking parameters were fixed at constant values between trials. As can be understood from the results of the trials set out in FIG. 11, and consistent with conventional wisdom indicating that polymeric members (454) cannot be laser marked, certain of the marking conditions either did not produce a visible mark (418) or generated a visible mark (418) but resulted in permeability or deformation of the polymeric members (454) which made each of these polymeric members (454) unsuitable for the intended use of containing biological materials. Unexpectedly, in a narrow range of conditions shown in FIG. 11, it was possible to laser mark (without creating permeability or deformation of the polymeric member (454)) this particular embodiment of a polymeric member (454) by utilizing a step size of 70 µm or 100 µm and respectively a power of between about 0.1% and 75% of 2 W or 100% of 2 W. It is interesting to note that at a step size of 100 µm no visible marking (418) occurred at less than 75% of 2 W power, while at a step size of 70 µm it was possible to visibly mark (418) each polymeric member (454) within the wide range of power between about 0.1% and about 75% of 2 W.

Again referring primarily to FIG. 11, in accordance with the procedure above-described six individual trials were conducted on a corresponding plurality of polymeric members (454) obtained from IMV Technologies, 10, rue Clemenceau, 61300 L'Aigle, France, having catalog number 5584 (Blue) (see key in FIG. 11 upper middle of each data grid). Fluence of laser beam pulses (409) was adjusted between 5% and 100% of 2 W and the step size was adjusted between about 40 µm and about 70 µm as above described to generate various laser marking conditions. All other parameters were fixed at constant values between trials. As can be understood from the results of the trials set out in FIG. 11, certain of the marking conditions either did not produce a visible mark (418) or generated a visible mark (418) but resulted in permeability or deformation of the polymeric members (454) that rendered those polymeric members (454) unsuitable for the intended use of containing biological materials. Again unexpectedly, in a narrow range of conditions, it was possible to laser mark this particular embodiment of a polymeric member (454) by utilizing a step size of 50 μm and a power of between about 5% and 50% of 2 W. A lack of predictability is evidenced by the step size and power useful in laser marking polymeric members (454) catalog number 5567 (Red) which failed to produce visible marks (418) on polymeric members (454) catalog number 5584 (Blue).

The remainder of the trials were performed in accordance with the procedure above-described on a variety of different polymeric members (454) obtained from IMV Technologies, 10, rue Clemenceau, 61300 L'Aigle, France, having catalog numbers 5565 (Clear), 5580 (Orange), 5575 (Yellow), and 5577 (Grey)(see the Key in FIG. 11). As to each particular embodiment of the polymeric member (454) the trial conditions which produced a visible mark (418) without resulting in permeability or deformation of the polymeric member substantially varied; however, unexpectedly as to each embodiment of polymeric member a narrow range of trial conditions allowed the polymeric member (454) to be visibly marked (418) by incidence of the laser beam (402) without resulting in permeability or deformation of the polymeric member.

The results of the thirty-seven trials evidence that the conditions under which a laser beam (402) can induce a visible mark (418) on the marking plane (412) of a polymeric member (454) can vary substantially and unpredictably between a plurality of polymeric members (454) differentiated by dispersed colorant (464) within the corresponding polymeric matrices (465). None-the-less, as to each embodiment of polymeric member (454), a narrow set of laser marking conditions can be established which allow visible marking (418) without resulting in permeability or deformation of each type of polymeric member (454).

One aspect relates to the desire to laser marked straws (461) quickly while maintaining straw integrity for holding biological materials. The described systems and methods relate to adjusting the irradiation dwell period (420) and fluence based on the characteristics of the straws (461) in order to reduce damage to straws (461) while producing visible marks (418). Additionally, laser fluence, step size and/or irradiation dwell period (420) can further be reduced and laser marking can further be improved by coordinating or matching additives, such as colorants (464) having electromagnetic radiation absorbance properties with lasers beams (402) of particular wavelengths. FIG. 11 demonstrates the ability to reduce both laser power and the time required by utilizing complimentary colorants (464) and laser sources (401). Specifically, laser sources (401) may have laser beam (402) wavelengths matched to certain electromagnetic radiation absorbance properties of the polymeric members (454) being marked. The process of marking with a laser, such as etching, results in both localized charring type "photo damage" and heat dissipation through a region which can result in warping and loss of integrity. The thirty-seven trials demonstrated that it may be desirable to coordinate marking materials and laser sources in a manner that tends to produce charring type of photo damage, as opposed to producing heat transference which may warp a straw.

The results of the thirty-seven trials indicate step size can be improved, straw marking times can be reduced and laser fluence can be reduced, each generally reducing straw (461) damage and warping by coordinating or matching an additive, such as a colorant (464), or dye, having electromagnetic radiation absorbance properties matched to the laser source (401). While some interplay exists between step size and laser fluence, there is level of unpredictability in producing visible marks (418) on thin polymeric members (454). However, a benefit can be seen for matching colorants (464) with electromagnetic radiation absorbance properties that peak at, or near, the wavelength of the laser source (401). Examples of desirable electromagnetic radiation absorbance properties can be a maximum electromagnetic radiation absorbance wavelength or a local maximum electromagnetic radiation absorbance wavelength. Colorants (464), or dyes, which are visible complimentary colors to the color of the laser wavelength may exhibit good absorbance properties at the wavelength of the laser source. In FIG. 12 a color wheel illustrates the primary and secondary colors and related complimentary colors.

FIG. 11 demonstrates improved straw (461) marking when straw (461) colors are selected corresponding to, or approximately matched to, the wavelength of the laser source (401). The trials demonstrate absorption of such matched lasers and straws (461) provide for the desired localized type of "photodamage" characterized by shallow divots and charring for improved contrast, whereas those laser emissions which are not so matched result in less localized affects resulting in deeper divots, as well as, more heat transferred to the surrounding area, and a greater tendency to warp the straws (461). Additionally, more power might be required to achieve the desired charring "photodamage," in unmatched straws and lasers compounding the tendency to warp the straws (461).

In particular, FIG. 11 illustrates results with good markings at low laser powers and at faster times for a 532 nm wavelength ("green") laser on red straws. Red and green can be considered complimentary colors, as a red dye exhibits good absorbance for light in the green range of the visible spectrum. Specifically, the red straw could be marked 2.4 seconds utilizing 75% 2 W power or with as little as 10 mW in 4.25 seconds. Even at 25% power the laser produced enough heat to warp the red straw in 6.6 seconds. In contrast, the yellow dye was not able to produce visible marks at 50 mW in 4.25 seconds. The orange straw, which would have electromagnetic radiation absorbance characteristics close to that of a red straw, produced visible marks at 50% power in 4.5 seconds. In further contrast, the clear straw did not warp until marking for 14 seconds.

Various embodiments described herein relate to methods emulating the behavior of the red straws subjected to the 532 nm (green) laser. With reference to FIG. 13, in which like parts are provided with the same character references, one such method can include the step of obtaining a polymeric member (454), where the polymeric member (454) is formed from a polymeric matrix (465) including an additive with electromagnetic radiation absorbance properties (471). The additive can be a dye or colorant (464), which can have good electromagnetic radiation absorbance at certain wavelengths and even a maximum electromagnetic radiation absorbance wavelength. The electromagnetic radiation absorbance properties of the additive (471) can be matched with the wavelength of the laser source (401), so the colorant (464) tends to absorb the laser energy well. This concept can be referred to as "impedance matching."

A marking plane (412) can be defined on the surface of the polymeric member (454). A laser beam (402) can be emitted from the laser source (401) and directed incident upon the marking plane (412) on the surface of the polymeric member (454). The matched laser beam (402) can then be optically focused incident upon the marking plane (412) on the surface of the polymeric member (454) to establish a laser beam spot (413) having a fixed dimensional boundary (414). Finally, the polymeric member (454) can be visibly marked on the marking plane (412).

Matching the laser source (401) with electromagnetic radiation absorbance properties of the additive (471) may include substantially matching the wavelength of the laser beam (402) with the maximum absorbance wavelength of the colorant (464), or dye, or with wavelengths at which the colorant (464) exhibits good electromagnetic radiation absorbance (such as a local maximum). This matching may occur within the visible light spectrum of about 400 nm-700 nm or in the ultra violet frequency range 250 nm-400 nm. As one example, the matching of the maximum absorbance wavelength of the colorant (464) and the laser beam (402) wavelength may occur within about 60 nm, or within about 40 nm. As another example, the matching of the wavelengths may broadly be considered selecting both laser beam (402) wavelengths and colorants (464) with maximum absorbance wavelengths characterized within the same family of primary or secondary colors. With reference to the visible color of the colorants (464), this matching may also be considered as selecting lasers characterized as primary or secondary colors which are complimentary to the visible colors of the colorants (464). Similarly, straws (461) may be selected for including dyes or colorants (464) which are complimentary in color to the wavelength of the laser source.

As another specific non-limiting example, the polymeric member (454) may be doped with an additive (471) that absorbs light well in the ultra violet frequency range. The polymeric member (454) may then be marked with a laser source (401) operating at a wavelength in ultra violet range, regardless of the color of the polymeric member (54). One example of a suitable laser operating is 150 mW laser available from Vanguard having a wavelength of about 355 nm. One example of an additive (471) is a colorant (464) which absorbs light in the ultra violet frequency range and may include photochromic dyes (473). Photochromic dyes (473) may be considered dyes which exhibit different light absorption or emission spectra in response to certain conditions. The exposure of the photochromic dye (473) to ultraviolet light, or natural light with an ultraviolet component, may be one such condition which varies the absorption or emission spectra of the dye (473). Photochromic dyes (473) may comprise dyes from the spiro-naphthoxazines and naphthopyrans families, which undergo physical changes to their chemical structure in response to particular frequencies of electromagnetic radiation including light in the ultraviolet frequency range and are generally characterized as shifting from transparent to a selected color, when activated. Photochromic dyes (473) of this nature are commercially available as Reversacol™ dyes from James Robinson Ltd., Huddersfield, United Kingdom, and are described in more detail in U.S. Pat. Nos. 5,559,231 and 6,303,673, each of which are incorporated herein by reference. These dyes may be incorporated into clear straws or straws with any basal color having a basal dye (475). As compared to the 532 nm "green laser", the 355 nm "UV" laser provides higher energy photons which are delivered at a greater frequency. The combination of higher energy photons and increased beam frequency may increase the resolution of the laser etching and reduce the time required to make a visible mark.

Additionally, 0.25 ml straws (461) may be constructed from a Polyethylene terephthalate PETG for its durable qualities. However, PETG is sensitive to ultra violet light and becomes brittle and opaque when exposed to sunlight for a long period. For this same reason, an ultra violet laser is expected to mark on PETG straws (461) with a high contrast. An ultra violet laser source (401) may be used for etching PETG straws (461) at increased speeds with reduced fluence. The use of ultra violet laser source (401) would additionally provide the benefit of requiring a substantially uniform fluence and irradiation dwell period (420) as compared to the 532 nm laser regardless of straw basal color because the basal colors would not demonstrate differences in the absorbance of the ultra violet laser. The addition of a photochromic dye (473) may further improve the ability to mark on PETG straws (461) with an ultra violet laser source (401), by further reducing the fluence required to make a visible mark.

As one example, the step of matching a colorant (464) with a laser source (401) may begin by selecting a commercially available laser such as a 266 nm, 355 nm 532 nm or 1064 nm Vanguard lasers at 150 mW or at 350 mW, available from Spectra Physics. The polymeric members (454), such as straws (461), may then be selected or produced having properties which tend to absorb the wavelength of visible or ultra violet light produced by the selected laser source (401). A colorant (464) may be dispersed in the polymeric matrix (465) of the polymeric member (454) for this purpose. As one example, polymeric members (454) may be selected having photochromic dyes (473) for use with the 266 nm and 355 nm lasers. As another example, polymeric members (454), which absorb green light, such as red polymeric members (454), may be paired with the lasers sources (401) operating a wavelengths characterized as green, such as 532 nm. Similarly, lasers sources (401) throughout the ultra violet and visible light spectrum may be selected and matched with complimentary polymeric members (454). Table 2 illustrates commercially available lasers sources (401) at common operations frequencies, although tunable lasers are also available which may achieve a range of wavelengths. Each listed laser serves only as an example and many other lasers and laser wavelengths are envisioned within the scope of this invention. In Table 2 the laser color is a generalization referencing either the primary, or secondary color to which the wavelength is the closest.

TABLE 2

| Laser | Wavelength (nm) | Laser Color | Complimentary Dye Color |
|---|---|---|---|
| Vanguard (nd: YAG)[1] | 266 nm | UV | Photochromic dye[3] |
| Vanguard (nd: YAG)[1] | 355 nm | UV | Photochromic dye[3] |
| 85/95 Argon[2] | 458 nm | Blue | Orange |
| 85/95 Argon[2] | 488 nm | Blue | Orange |
| Vanguard (nd: YAG)[1] | 532 nm | Green | Red |
| 85/95 Argon[2] | 514 nm | Green | Red |
| Copper Vapor Laser | 578 | Yellow | Violet |
| Helium-Neon Laser[1] | 633 nm | Red | Green |
| 85/95 Krypton[2] | 676 | Red | Green |
| Vanguard (nd: YAG)1 | 1064 nm | Infrared | — |

[1]available from Spectra Physics
[2]available from Lexel Lasers
[3]available from James Robinson Ltd.

In another embodiment, the polymeric members (454) may be constructed from a polymeric matrix (465) with a colorant (464), or dye, dispersed for achieving a desired color. The laser source (401) may then be matched as complimentary to the color of the polymeric member (454).

In one embodiment, the fluence of the laser beam (402) can be adjusted to produce a visible mark (418) on the matched polymeric member (477). The fluence can be minimized in order to reduce warping of the matched polymeric member (477) while still producing a visible mark (418). The fluence may be adjusted by adjusting the irradiation dwell period (420) and may be adjusted to speed up marking polymeric members (454). The output energy of the laser source (401) may also be reduced to adjust the fluence of the laser beam (402).

Photochromic Dyes

With reference to FIG. 14, another method of laser etching a straw may include the use of a polymeric member (454) formed from a polymeric matrix (465) including a photochromic dye (473) which can be transitioned from an inactive state to an activated state. The photochromic dye (473) may remain relatively colorless in the inactive state and can have a selected visible color in the activated state. The photochromic dye (473) can be selected and matched such that the visible color in the active state is complimentary to the laser source (401) used for marking. Such dyes tend to have good absorbance in at least some portion of the ultra violet frequency range, but may also have good absorbance, or a local maximum absorbance wavelength, which can be matched with the wavelength of the laser source (401).

The method may continue with the activation of the photochromic dye (473). Once activated, the photochromic dye (473) may either transition from a transparent polymeric member (454) to a preselected color, or may have a combined effect with a basal dye (475) in the polymeric matrix (465) and alter the existing color of a polymeric member (454). In either event, when the visible color of the activated photochromic dye (473) is complementary to the wavelength of the laser source (401), the activated polymeric member (479) may demonstrate an improved absorbance for the laser source (401) resulting in improved marking.

The method can continue with defining a marking plane (412) on the surface of the polymeric member (454) and matching a laser source (401) with an electromagnetic radiation absorbance property of the photochromic dye (473) in the activate state and activating the photochromic dye (473) within the polymeric member (454) defining a marking period. The period during which the photochromic dye (473) is activated can define a marking period and may be achieved with a ultra violet lamp, an arc lamp, or another source of electromagnetic radiation (481) producing activation energy (483) depending upon the activation properties of the photochromic dye (473).

The laser source (401) can emit a laser beam (402) directed incident upon the marking plane (412) on the surface of the polymeric member (454) during the marking period. The laser beam (402) can be optically focused incident upon the marking plane (412) on the surface of the polymeric member (454) to establish a laser beam spot (413) having a fixed dimensional boundary resulting in visibly marking the polymeric member (454) on the marking plane (412) on the surface of the polymeric member (454) during the marking period.

The laser source (401) may be selected with a wavelength in the visible light frequency range of about 400 nm to about 700 nm and may be matched with the maximum absorption wavelength of the photochromic dye (473) in the activated state within about 60 nm, or within about 40 nm. Table 3 below illustrates the Reversacol™ product line of photochromic dyes and their maximum absorbance wavelengths in the activated state.

TABLE 3

| Name | λ max (nm) - activated |
|---|---|
| Corn Yellow | 455 |
| Rush Yellow | 430 |
| Sunflower | 445 |
| Solar Yellow | 430 |
| Flame | 475 |
| Poppy | 500 |
| Cardinal | 505 |
| Cherry | 520 |
| Berry Red | 490 |
| Claret | 545 |
| Ruby | 490 |
| Amethyst | 560 |
| Plum Red | 555 |
| Palatinate Purple | 595 |
| Storm Purple | 585 |
| Lilac | 540 |
| Oxford Blue | 570 |
| Velvet Blue | 570 |
| Sea Green | 635 |
| Aqua Green | 610 |
| Heather | 476, 546 |
| Misty Grey | 485, 570 |
| Midnight Grey | 485, 570 |
| Graphite | 485, 585 |

The photochromic dye (473) may be characterized as having two local maxima in the light absorption spectra. The first local maxima may correspond to the ultra violet frequency range, indicating the energy which is absorbed in the reaction that causes a color shift. The second local maximum may be characteristic of the activated visible color. A photochromic dye may be matched directly to a laser operating in the ultra violet frequency range, or may have an activated state matched to a particular laser. In the activated state, such a photochromic dye would be tinted with a color that is complementary to the color of the laser source (401). Examples, as demonstrated in FIG. 12, include: a red activated photochromic dye and a green laser; a blue activated photochromic dye and an orange laser; a yellow activated photochromic dye and a violet laser; a green activated photochromic dye and a red laser; an orange activated photochromic dye and a blue laser; and a violet activated photochromic dye and a yellow laser.

As one non-limiting example, a straw containing any basal colorant may additionally be doped with the photochromatic colorant Plum Red available under the trade name Reversacol™ from James Robinson (UK). The photochromatic dye may then be activated with an ultra violet lamp or other source of ultra violet light. Once activated, a 532 nm "green" laser, such as a Vangaurd 532, may be used to produce a visible mark on the straw. A straw doped with a photochromic dye matched to the marking laser may be printed quicker and with less power than straws having unmatched basal dyes without photochromic additives.

In one embodiment, the step of activation may be performed by the marking laser (401). As a non-limiting example, a green laser used for marking may interact with the polymeric member (454) to produce frequency doubled wavelengths of light. In such an embodiment, a green laser operating at 532 nm may be frequency doubled to produce some light at a near ultraviolet wavelength 266 nm. The number of photons frequency doubled in this manner may be a small fraction of the total photons, but may be sufficient to activate a photochromic dye (473) within the polymeric member (454). In such an embodiment, a green laser may both mark a polymeric member (454) and activate the photochromic dye (473) in the polymeric member (454).

Certain embodiments also relate to the apparatus of a polymeric member (454) seen in FIGS. 13 and 14 for storing and transporting biological material. The polymeric member (454) may include a axial body (455) which defines an axial passage (456) between a pair of body ends (457)(458), and in particular a cylindrical body (459) defining a cylindrical passage (460). The cylindrical body (460) may have an exterior surface and may be formed from a polymeric matrix (465) including a photochromic dye (473). The photochromic dye (473) may be selected to change the color of the polymeric member (454) in visible light or under ultra violet light. In one embodiment, the polymeric member (454) may be activated by ultra violet light, and may also serve to protect the biological materials from ultra violet exposure. The apparatus may further include a plug for sealing the substantially tubular polymeric member.

The polymeric member may comprise a straw (461) for storing or transporting biological materials including those selected from: an amount of semen, an ova, ovum, an enucleated cell, a plurality of sperm cells, an embryo, a plurality of sex-selected sperm cells, a sex-selected embryo, a pathogen, a bacteria, and a virus. The straw (461) may have a thickness between about 0.1 mm and 0.2 mm and may be constructed from a polyvinyl chloride or a polyethylene terephthalate. In some embodiments materials may be marked having thicknesses less than 0.5 mm.

Methods of Laser Printing on Metallic Surface

The benefits of a two-dimensional bar code provided herein give rise to previously unrecognized problems and challenges. Namely, the canes in the AI industry, and tabs which may be attached to those canes, may be metallic. As such, neither the canes nor the cane tabs provide a surface that allows either quick laser printing or a desirable resolution for two-dimensional barcodes. Laser printing on a metallic surface may be achieved by basically charring the metal. The laser power required to produce such charring may not be well localized due to the thermal conductivity or metals in particular and this may result in an undesirable resolution. Additionally, the time required to produce such charring may render the entire printing process undesirable for any commercial application.

Surprisingly, improved resolution has been achieved in printing metallic surfaces and curved metallic surfaces, such as canes used in the AI industry. Additionally, various printing methods described below have reduced printing times to Improved resolution and speed allows the possibility of printing two-dimensional bar codes which contain more information than was previously achieved.

In one embodiment, an improved printing speed and resolution has been achieved by applying a first coating to a metallic surface. As an illustrative embodiment, a spray paint maybe employed. However, other coatings and other means for applying the coatings may also be utilized.

However applied, the first coating may be covered in a second coating. The first coating may be black or another dark color, while the second, or outer, coating may be a lighter coating. Once each coating is sufficiently dry, the second coating may be laser etched with sufficient precision to expose the first coating, but not the metallic surface. A laser, such as the 5 watt laser previously described may quickly, and with much less power etch away selected portions of the outer coating, exposing the inner coating. In this manner, symbols letters, 1D barcodes, and 2 D barcodes maybe be quickly laser printed onto the surface of the object being printed.

It should be appreciated, that many colors may be used for each coating, so long as they provide a contrast which is detectable by a bar code reader. For example, the first coating may be a light color, and second outer coating may be a darker color.

Example 1

A two-dimensional bar code known as a DataMatrix 2D barcode was generated in the form of 16 rows and 48 columns for the following sequence of 57 characters: "aA1bB2cC3dD4eE5fF6gG7hHijJ8kK9lL0mM1nN2oO3p-P4qQ5rR6sS7tT8." The pattern for this barcode is illustrated in FIG. 5A. From the pattern a representation of the barcode was formulated to fit on a 1.56 mm high×3.51 mm wide marking plane having 16 rows and 48 columns. A Laser Marking System (U-5G) in conjunction with a 254 mm F-Theta Focusing Lens was used to visibly produce the two-dimensional bar code by marking a plurality of pixel locations on the marking plane. The U-G5 was set to Passes: 1, Power: 60, Pulses: 1, Speed: 100, Step Size: 50 for printing on a cryopreservation straw (0.25 mL, transparent pistachio, catalog number 13407/0204, lot number 1251936/1-1, Minitüb GmbH, Tiefenbach, Germany). The resulting two-dimensional bar code on the straw was read correctly with an iPod Touch 4 (Apple, Inc. Cupertino, Calif., USA) equipped with a magnification lens (Wide+Macro Lens, SKINA® W-67, Shanghai SKINA Digital Technology Co., Ltd, Shanghai, China) using 2D scanning software App (NeoReader v4.4.0, NeoMedia Technologies, Inc., Boulder, Colo., USA).

Example 2

A two-dimensional bar code known as a DataMatrix 2D barcode was generated in the form of 16 rows and 48 columns for the following sequence of 57 characters: "aA1bB2cC3dD4eE5fF6gG7hHijJ8kK9lL0mM1nN2oO3p-P4qQ5rR6sS7tT8." The pattern for this barcode is illustrated in FIG. 5A. From the pattern a representation of the barcode was formulated to fit on a 1.56 mm high×3.51 mm wide marking plane having 16 rows and 48 columns. A Laser Marking System (U-5G) in conjunction with a 254 mm F-Theta Focusing Lens was used to visibly produce the two-dimensional bar code by marking a plurality of pixel locations on the marking plane. The U-G5 was set to Passes: 1, Power: 60, Pulses: 1, Speed: 100, Step Size: 50 for printing on a cryopreservation straw (0.25 mL, yellow, catalog number 13407/0090, lot number 1250367/1, Minitüb GmbH, Tiefenbach, Germany). The resulting two-dimensional bar code on the straw was read correctly with an iPod Touch 4 (Apple, Inc. Cupertino, Calif., USA) equipped with a magnification lens (Wide+Macro Lens, SKINA® W-67, Shanghai SKINA Digital Technology Co., Ltd, Shanghai, China) using 2D scanning software App (NeoReader v4.4.0, NeoMedia Technologies, Inc., Boulder, Colo., USA).

Example 3

A two-dimensional bar code known as a DataMatrix 2D barcode was generated in the form of 16 rows and 48 columns for the following sequence of 57 characters: "aA1bB2cC3dD4eE5fF6gG7hHijJ8kK9lL0mM1nN2oO3p-P4qQ5rR6sS7tT8." The pattern for this barcode is illustrated in FIG. 5A. From the pattern a representation of the barcode was formulated to fit on a 1.56 mm high×3.51 mm wide marking plane having 16 rows and 48 columns. A Laser Marking System (U-5G) in conjunction with a 254 mm F-Theta Focusing Lens was used to visibly produce the two-dimensional bar code by marking a plurality of pixel locations on the marking plane. The U-G5 was set to Passes: 1, Power: 40, Pulses: 1, Speed: 100, Step Size: 50 for printing on a cryopreservation straw (0.25 mL, beige, catalog number 13407/0180, lot number 1250370/1-1, Minitüb GmbH, Tiefenbach, Germany). The resulting two-dimensional bar code on the straw was read correctly with an iPod Touch 4 (Apple, Inc. Cupertino, Calif., USA) equipped with a magnification lens (Wide+Macro Lens, SKINA® W-67, Shanghai SKINA Digital Technology Co., Ltd, Shanghai, China) using 2D scanning software App (NeoReader v4.4.0, NeoMedia Technologies, Inc., Boulder, Colo., USA).

Figure 5B:
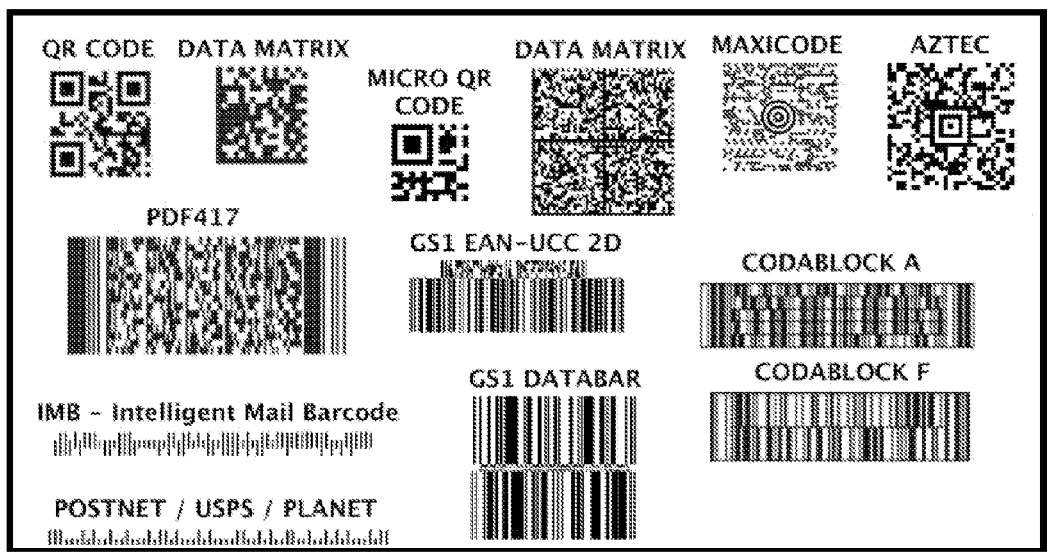
FIG. 5B illustrates additional embodiments of two-dimensional bar codes in accordance with certain embodiments described herein.

As can be easily understood from the foregoing, the basic concepts of the present invention may be embodied in a variety of ways. By way of a non-limiting example, various two-dimensional barcodes, such as those depicted in FIG. 5B may also be used in accordance with certain embodiments described herein.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A method comprising:
   processing reproductive cells derived from an identified source;
   matching a laser wavelength to a maximum electromagnetic radiation absorbance wavelength or a local maximum electromagnetic radiation absorbance wavelength of a photochromic dye dispersed in a straw, wherein the straw is no larger than about 2 mm in diameter and no longer than about 133 mm in length;
   laser etching a two-dimensional bar code into the straw with the impedance matched laser, wherein the laser etched two-dimensional bar code encodes between 30 and 229 characters, and wherein marked portions of the laser etched two-dimensional barcode modify the surface depth and color of the exterior surface of the straw; and
   storing processed reproductive cells from the identified source in the marked straw, wherein the laser etched two-dimensional bar code identifies the source of the reproductive cells.

2. The method of claim 1, wherein the straw comprises more than one straw.

3. The method of claim 2, wherein the laser etched two-dimensional bar code is scannable by a portable device with a magnifying lens.

4. The method of claim 2, wherein the more than one straw comprises multiple straws and wherein the laser etched two-dimensional bar code on each straw encodes a unique serial number.

5. The method of claim 4, wherein each straw in a lot is associated with specified set of canes for storage.

6. The method of claim 5, wherein the set of canes are marked with cane identification numbers encoded on bar codes.

7. The method of claim 6, wherein the step of associating straws with a set of canes further comprises scanning the bar code of each cane and scanning the bar code of each straw placed therein to index each scanned straw with each cane in a database.

8. The method of claim 2, wherein the step of storing the processed reproductive cells in the straw comprises filling marked straws with processed sperm.

9. The method of claim 8, further comprising:
   freezing a marked straw;
   thawing a frozen marked straw;
   scanning the marked straw; and
   performing an artificial insemination or an in vitro fertilization with sperm from the thawed straw.

10. The method of claim 8, further comprising the step of: tracking the progress of the insemination and recording quality control data and/or fertility data.

11. The method of claim 8, further comprising the step of: associating the thawed straw with an intended recipient and verifying the recipient after scanning the marked straw.

12. The method of claim 2 further comprising the steps of:
receiving an order for straws of processed animal sperm from the identified source;
querying an inventory of frozen straws for the number of straws available from the identified source;
filling the order; and
scheduling collections from the identified source to refill the inventory.

13. The method of claim 12, wherein collections are routinely scheduled.

14. The method of claim 12, wherein collections are scheduled once inventory drops below a predetermined volume threshold.

15. The method of claim 12, wherein inventory in the form of straws are associated in groups in a canes, wherein said canes are marked with two-dimensional barcodes, and the associated groups of straws are moved in and out of inventory by scanning the canes.

16. The method of claim 1, wherein the laser is focused to a beam spot between 25 µm and 80 µm in diameter.

17. The method of claim 1, wherein the laser is operated at a power between 0.1 Watts and 3.5 Watts.

18. The method of claim 1, wherein the photochromatic dye is impedance matched to the laser utilized in the step of marking.

19. The method of claim 1, further comprising marking a goblet or a cane that holds a plurality of straws, wherein the marking on the goblet or cane indicates the source of materials contained within an associated plurality of straws.

20. The method of claim 19, further comprising moving the associated plurality of straws into and out of inventory by scanning the laser etched two-dimensional bar code on the goblet or cane.

21. The method of claim 1, wherein the step of marking a straw with a laser etched two-dimensional bar code further comprises:
establishing a plurality of characters, wherein the plurality of characters encode information identifying the contents to be stored in the straw;
generating a two-dimensional bar code encoding the established characters;
defining a representation of the two-dimensional bar code as a plurality of pixel locations;
defining a marking plane on a limited printing surface of the straw;
establishing a laser step size;
establishing a laser power;
producing visible marks on the straw which correspond to the plurality of pixel locations representing the two-dimensional bar code.

22. The method of claim 21, wherein the dimensions of the laser etched two-dimensional bar code are about 1.56 mm by 3.51 mm.

23. The method of claim 21, wherein the straw remains impermeable to fluids after marking and the laser etched two-dimensional barcode is readable by a portable device having a magnification lens.

24. The method of claim 1, wherein the reproductive cells comprise sperm and wherein the step of processing further comprises the step of sex sorting sperm.

25. The method of claim 1, wherein reproductive cells comprise sperm and the laser etched two-dimensional bar code on the container comprises one or more of:
an encoded stud, breed, sire identification number
an encoded sire's registered name;
an encoded freeze date, or an encoded lot number, or an encoded batch number, or an encoded freeze code number; or
an encoded international stud code.

26. The method of claim 1, further comprising the step of scanning the etching laser over a marking area to produce the laser etched two-dimensional bar code.

27. A straw for containing a biological material comprising:
an axial body defining an axial passage between a pair of body ends, the axial body having an exterior surface, an interior surface and a thickness between the exterior surface and the interior surface, wherein the thickness between the exterior surface and the interior surface is between about 0.1 mm and about 0.3 mm, and wherein the straw which is no larger than about 2 mm in diameter and no longer than about 133 mm in length;
a dispersed photochromic dye having a maximum electromagnetic radiation absorbance wavelength or a local maximum electromagnetic radiation absorbance wavelength; and
a laser etched two-dimensional bar code on the exterior surface of the axial body formed by a laser having a wavelength matched to the maximum electromagnetic radiation absorbance wavelength or a local maximum electromagnetic radiation absorbance wavelength of the dispersed photochromic dye, wherein the laser etched two-dimensional bar code encodes between 30 and 229 characters, and wherein marked portions of the laser etched two-dimensional barcode modify the surface depth and color of the exterior surface of the straw while the straw remains unwarped and impermeable to fluids.

28. The straw of claim 27, wherein the height of the laser etched two-dimensional bar code is between about 1.25 mm and 1.75 mm and wherein the length of the laser etched two-dimensional bar code is between about 2.5 mm and 4.5 mm.

29. The straw of claim 27, wherein the dimensions of the laser etched two-dimensional bar code are about 1.56 mm by about 3.51 mm.

30. The straw of claim 27, wherein the laser etched two-dimensional bar code on each sealable container comprises a unique serial number.

31. The straw of claim 27, wherein each sealable container marked with a laser etched two-dimensional bar code is additionally marked with identifying information in alphanumeric print by the laser.

32. The straw of claim 27, further comprising plugs for sealing the axial passage of the straw and sperm sealed within the axial passage of the straw.

33. The straw of claim 27, wherein the laser having a wavelength matched to the maximum electromagnetic radiation absorbance wavelength or a local maximum electromagnetic radiation absorbance wavelength of the dispersed photochromic dye comprises a scanning laser.

* * * * *